(12) United States Patent
Galasso et al.

(10) Patent No.: US 11,875,887 B2
(45) Date of Patent: Jan. 16, 2024

(54) METHODS AND APPARATUS FOR VIRTUAL COMPETITION

(71) Applicant: Fox Factory, Inc., Duluth, GA (US)

(72) Inventors: Mario Galasso, Sandy Hook, CT (US); Wesley E. Allinger, Santa Cruz, CA (US); David M. Haugen, Pacific Grove, CA (US); Robert David Kaswen, Watsonville, CA (US); Mark Stephen Fitzsimmons, Gilroy, CA (US)

(73) Assignee: Fox Factory, Inc., Duluth, GA (US)

( * ) Notice: Subject to any disclaimer, the term of this patent is extended or adjusted under 35 U.S.C. 154(b) by 0 days.

(21) Appl. No.: 17/348,441

(22) Filed: Jun. 15, 2021

(65) Prior Publication Data

US 2021/0313038 A1 Oct. 7, 2021

Related U.S. Application Data

(60) Continuation of application No. 16/388,732, filed on Apr. 18, 2019, now Pat. No. 11,043,294, which is a
(Continued)

(51) Int. Cl.
*A63B 69/16* (2006.01)
*G16H 20/30* (2018.01)
(Continued)

(52) U.S. Cl.
CPC .............. *G16H 20/30* (2018.01); *A63B 22/06* (2013.01); *A63B 24/0021* (2013.01);
(Continued)

(58) Field of Classification Search
CPC ...... G16H 20/30; G16H 40/67; A63F 13/216; A63F 13/525; A63F 9/143; G06F 16/29; A63B 22/06; A63B 24/0021; A63B 24/0062; A63B 24/0084; A63B 69/16; A63B 71/0622; G06Q 30/02
See application file for complete search history.

(56) References Cited

U.S. PATENT DOCUMENTS

| 1,923,011 A | 8/1933 | Moulton |
| 1,948,600 A | 2/1934 | Templeton |

(Continued)

FOREIGN PATENT DOCUMENTS

| AU | 2006222732 A1 | 10/2006 |
| CA | 2323492 A1 | 9/1999 |

(Continued)

OTHER PUBLICATIONS

English language abstract for EP 0207409 (no date).
(Continued)

*Primary Examiner* — Steven J Hylinski

(57) ABSTRACT

A system configured to be coupled with a participant of an activity. The system comprises: a participant activity monitoring unit configured for monitoring a performance of the activity by the participant; an activity information module configured for storing performance information corresponding to the activity; and a participant performance correlator configured for delivering comparative performance data based on the monitored performance of the activity by the participant and the stored performance information.

1 Claim, 10 Drawing Sheets

Related U.S. Application Data division of application No. 16/016,444, filed on Jun. 22, 2018, now Pat. No. 10,537,790, which is a continuation of application No. 14/804,144, filed on Jul. 20, 2015, now Pat. No. 10,029,172, which is a continuation of application No. 12/626,384, filed on Nov. 25, 2009, now Pat. No. 9,108,098.

(60) Provisional application No. 61/117,608, filed on Nov. 25, 2008.

(51) Int. Cl.

| | | |
|---|---|---|
| A63F 13/216 | (2014.01) | |
| A63F 13/525 | (2014.01) | |
| A63F 9/14 | (2006.01) | |
| A63B 22/06 | (2006.01) | |
| G06F 16/29 | (2019.01) | |
| A63B 24/00 | (2006.01) | |
| G16H 40/67 | (2018.01) | |
| G06Q 30/0251 | (2023.01) | |
| A63B 71/06 | (2006.01) | |
| G06Q 30/02 | (2023.01) | |

(52) U.S. Cl.
CPC ...... *A63B 24/0062* (2013.01); *A63B 24/0084* (2013.01); *A63B 69/16* (2013.01); *A63B 71/0622* (2013.01); *A63F 9/143* (2013.01); *A63F 13/216* (2014.09); *A63F 13/525* (2014.09); *G06F 16/29* (2019.01); *G06Q 30/02* (2013.01); *G06Q 30/0251* (2013.01); *G06Q 30/0252* (2013.01); *G06Q 30/0255* (2013.01); *G06Q 30/0265* (2013.01); *G06Q 30/0269* (2013.01); *G16H 40/67* (2018.01); A63B 2024/0009 (2013.01); A63B 2024/0012 (2013.01); A63B 2024/0025 (2013.01); A63B 2024/0068 (2013.01); A63B 2071/0638 (2013.01); A63B 2071/0691 (2013.01); A63B 2220/12 (2013.01); A63B 2220/14 (2013.01); A63B 2220/20 (2013.01); A63B 2220/30 (2013.01); A63B 2220/51 (2013.01); A63B 2220/56 (2013.01); A63B 2220/805 (2013.01); A63B 2220/806 (2013.01); A63B 2225/50 (2013.01); A63B 2225/54 (2013.01); A63B 2230/00 (2013.01); A63B 2230/06 (2013.01); A63F 2300/6661 (2013.01)

(56) References Cited

U.S. PATENT DOCUMENTS

| | | |
|---|---|---|
| 2,259,437 A | 10/1941 | Dean |
| 2,492,331 A | 12/1949 | Spring |
| 2,540,525 A | 2/1951 | Howarth et al. |
| 2,697,600 A | 12/1954 | Gregoire |
| 2,705,119 A | 3/1955 | Ingwer |
| 2,784,962 A | 3/1957 | Sherburne |
| 2,879,971 A | 3/1959 | Demay |
| 2,991,804 A | 7/1961 | Merkle |
| 3,085,530 A | 4/1963 | Williamson |
| 3,087,583 A | 4/1963 | Bruns |
| 3,206,153 A | 9/1965 | Burke |
| 3,284,076 A | 11/1966 | Gibson |
| 3,528,700 A | 9/1970 | Janu et al. |
| 3,560,033 A | 2/1971 | Barkus |
| 3,575,442 A | 4/1971 | Elliott et al. |
| 3,603,575 A | 9/1971 | Arlasky et al. |
| 3,650,033 A | 3/1972 | Behne et al. |
| 3,701,544 A | 10/1972 | Stankovich |
| 3,784,228 A | 1/1974 | Hoffmann et al. |
| 3,830,482 A | 8/1974 | Norris |
| 3,903,613 A | 9/1975 | Bisberg |
| 4,036,335 A | 7/1977 | Thompson et al. |
| 4,103,881 A | 8/1978 | Simich |
| 4,348,016 A | 9/1982 | Milly |
| 4,366,969 A | 1/1983 | Benya et al. |
| 4,474,363 A | 10/1984 | Numazawa et al. |
| 4,630,818 A | 12/1986 | Saarinen |
| 4,634,142 A | 1/1987 | Woods et al. |
| 4,647,068 A | 3/1987 | Asami et al. |
| 4,655,440 A | 4/1987 | Eckert |
| 4,657,280 A | 4/1987 | Ohmori et al. |
| 4,732,244 A | 3/1988 | Verkuylen |
| 4,744,444 A | 5/1988 | Gillingham |
| 4,773,671 A | 9/1988 | Inagaki |
| 4,830,395 A | 5/1989 | Foley |
| 4,836,578 A | 6/1989 | Soltis |
| 4,938,228 A | 7/1990 | Righter |
| 4,949,262 A | 8/1990 | Buma et al. |
| 4,949,989 A | 8/1990 | Kakizaki et al. |
| 4,984,819 A | 1/1991 | Kakizaki et al. |
| 5,027,303 A | 6/1991 | Witte |
| 5,031,455 A | 7/1991 | Cline |
| 5,044,614 A | 9/1991 | Rau |
| 5,060,959 A | 10/1991 | Davis et al. |
| 5,074,624 A | 12/1991 | Stauble et al. |
| 5,094,325 A | 3/1992 | Smith |
| 5,105,918 A | 4/1992 | Hagiwara et al. |
| 5,152,547 A | 10/1992 | Davis |
| 5,203,584 A | 4/1993 | Butsuen et al. |
| 5,236,169 A | 8/1993 | Johnsen et al. |
| 5,265,902 A | 11/1993 | Ewis |
| 5,283,733 A | 2/1994 | Colley |
| 5,335,188 A | 8/1994 | Brisson |
| 5,348,112 A | 9/1994 | Vaillancourt |
| 5,390,949 A | 2/1995 | Naganathan et al. |
| 5,467,274 A | 11/1995 | Vax |
| 5,503,258 A | 4/1996 | Clarke et al. |
| 5,542,150 A | 8/1996 | Tu |
| 5,551,674 A | 9/1996 | Johnsen |
| 5,553,836 A | 9/1996 | Ericson |
| 5,592,401 A | 1/1997 | Kramer |
| 5,598,337 A | 1/1997 | Butsuen et al. |
| 5,642,285 A | 6/1997 | Woo et al. |
| 5,697,477 A | 12/1997 | Hiramoto et al. |
| 5,722,645 A | 3/1998 | Reitter |
| 5,802,492 A | 9/1998 | Delorme et al. |
| 5,803,443 A | 9/1998 | Chang |
| 5,816,281 A | 10/1998 | Mixon |
| 5,826,935 A | 10/1998 | Defreitas et al. |
| 5,828,843 A | 10/1998 | Samuel et al. |
| 5,829,733 A | 11/1998 | Becker |
| 5,850,352 A | 12/1998 | Moezzi et al. |
| 5,853,071 A | 12/1998 | Robinson |
| 5,884,921 A | 3/1999 | Katsuda et al. |
| 5,888,172 A | 3/1999 | Andrus et al. |
| 5,954,318 A | 9/1999 | Kluhsman |
| 5,971,116 A | 10/1999 | Franklin |
| 5,999,868 A | 12/1999 | Beno et al. |
| 6,002,982 A | 12/1999 | Fry |
| 6,013,007 A | 1/2000 | Root et al. |
| 6,017,047 A | 1/2000 | Hoose |
| 6,035,979 A | 3/2000 | Forster |
| 6,050,583 A | 4/2000 | Bohn |
| 6,058,340 A | 5/2000 | Uchiyama et al. |
| 6,073,736 A | 6/2000 | Franklin |
| 6,105,988 A | 8/2000 | Turner et al. |
| 6,135,434 A | 10/2000 | Marking |
| 6,152,856 A | 11/2000 | Studor et al. |
| 6,023,241 A | 12/2000 | Clapper |
| 6,219,045 B1 | 4/2001 | Eahy et al. |
| 6,244,398 B1 | 6/2001 | Girvin et al. |
| 6,249,241 B1 | 6/2001 | Jordan et al. |
| 6,254,067 B1 | 7/2001 | Yih |
| 6,282,362 B1 | 8/2001 | Murphy et al. |
| 6,311,962 B1 | 11/2001 | Marking |
| 6,336,648 B1 | 1/2002 | Bohn |
| 6,343,807 B1 | 2/2002 | Rathbun |
| 6,359,837 B1 | 3/2002 | Tsukamoto et al. |
| 6,360,857 B1 | 3/2002 | Fox et al. |

(56) References Cited

U.S. PATENT DOCUMENTS

| | | |
|---|---|---|
| 6,378,816 B1 | 4/2002 | Pfister |
| 6,378,885 B1 | 4/2002 | Ellsworth et al. |
| 6,389,341 B1 | 5/2002 | Davis |
| 6,390,747 B1 | 5/2002 | Commins |
| 6,412,788 B1 | 7/2002 | Ichimaru |
| 6,418,360 B1 | 7/2002 | Spivey et al. |
| 6,427,812 B2 | 8/2002 | Crawley et al. |
| 6,434,460 B1 | 8/2002 | Uchino et al. |
| 6,450,922 B1 | 9/2002 | Henderson et al. |
| 6,458,060 B1 | 10/2002 | Watterson et al. |
| 6,539,336 B1 | 3/2003 | Vock et al. |
| 6,592,136 B2 | 7/2003 | Becker et al. |
| 6,609,686 B2 | 8/2003 | Malizia |
| 6,623,389 B1 | 9/2003 | Campagnolo |
| 6,701,234 B1 | 3/2004 | Vogelsang et al. |
| 6,732,033 B2 | 5/2004 | LaPlante et al. |
| 6,741,790 B1 | 5/2004 | Burgess |
| 6,741,864 B2 | 5/2004 | Wilcock et al. |
| 6,744,403 B2 | 6/2004 | Milnes et al. |
| 6,837,827 B1 | 1/2005 | Lee et al. |
| 6,853,955 B1 | 2/2005 | Burrell et al. |
| 6,857,625 B2 | 2/2005 | Löser et al. |
| 6,863,291 B2 | 3/2005 | Miyoshi |
| 6,868,338 B1 | 3/2005 | Elliott |
| 6,885,971 B2 | 4/2005 | Vock et al. |
| 6,902,513 B1 | 6/2005 | McClure et al. |
| 6,904,160 B2 | 6/2005 | Burgess |
| 6,906,643 B2 | 6/2005 | Samadani et al. |
| 6,914,626 B2 | 7/2005 | Squibbs |
| 6,921,351 B1 | 7/2005 | Hickman et al. |
| 6,928,230 B2 | 8/2005 | Squibbs |
| 6,935,157 B2 | 8/2005 | Miller |
| 6,950,519 B2 | 9/2005 | Rhoads |
| 6,991,076 B2 | 1/2006 | McAndrews |
| 7,025,367 B2 | 4/2006 | McKinnon et al. |
| 7,046,285 B2 | 5/2006 | Miyagi et al. |
| 7,061,510 B2 | 6/2006 | Rhoads |
| 7,076,351 B2 | 7/2006 | Hamilton et al. |
| 7,128,192 B2 | 10/2006 | Fox |
| 7,128,693 B2 | 10/2006 | Brown et al. |
| 7,135,794 B2 | 11/2006 | Kühnel |
| 7,149,961 B2 | 12/2006 | Harville et al. |
| 7,163,222 B2 | 1/2007 | Becker et al. |
| 7,166,062 B1 | 1/2007 | Watterson et al. |
| 7,166,064 B2 | 1/2007 | Ashby et al. |
| 7,204,466 B2 | 4/2007 | Hsieh |
| 7,217,224 B2 | 5/2007 | Thomas |
| 7,239,760 B2 | 7/2007 | Di Bernardo et al. |
| 7,254,516 B2 | 8/2007 | Case, Jr. et al. |
| 7,255,210 B2 | 8/2007 | Arsson et al. |
| 7,287,760 B1 | 10/2007 | Quick et al. |
| 7,289,138 B2 | 10/2007 | Foote et al. |
| 7,292,867 B2 | 11/2007 | Werner et al. |
| 7,293,764 B2 | 11/2007 | Fang |
| 7,306,206 B2 | 12/2007 | Turner |
| 7,316,406 B2 | 1/2008 | Kimura et al. |
| 7,330,511 B2 | 2/2008 | Maltagliati et al. |
| 7,333,054 B2 | 2/2008 | Ueno et al. |
| 7,363,129 B1 | 4/2008 | Barnicle et al. |
| 7,374,028 B2 | 5/2008 | Fox |
| 7,397,355 B2 | 7/2008 | Tracy |
| 7,415,336 B1 | 8/2008 | Burch et al. |
| 7,451,056 B2 | 11/2008 | Flentov et al. |
| 7,454,090 B2 | 11/2008 | Wilcock et al. |
| 7,469,910 B2 | 12/2008 | Münster et al. |
| 7,480,512 B2 | 1/2009 | Graham et al. |
| 7,484,603 B2 | 2/2009 | Fox |
| 7,490,705 B2 | 2/2009 | Fox |
| 7,503,878 B1 | 3/2009 | Amsbury et al. |
| 7,519,327 B2 | 4/2009 | White |
| 7,526,718 B2 | 4/2009 | Samadani et al. |
| 7,558,313 B2 | 7/2009 | Feher |
| 7,558,574 B2 | 7/2009 | Feher et al. |
| 7,559,877 B2 | 7/2009 | Parks et al. |
| 7,566,290 B2 | 7/2009 | Lee et al. |
| 7,581,743 B2 | 9/2009 | Graney et al. |
| 7,602,301 B1 | 10/2009 | Stirling et al. |
| 7,607,243 B2 | 10/2009 | Berner et al. |
| 7,631,882 B2 | 12/2009 | Hirao et al. |
| 7,673,936 B2 | 3/2010 | Hsu et al. |
| 7,684,911 B2 | 3/2010 | Seifert et al. |
| 7,694,987 B2 | 4/2010 | McAndrews |
| 7,698,101 B2 | 4/2010 | Alten et al. |
| 7,699,753 B2 | 4/2010 | Daikeler et al. |
| 7,703,585 B2 | 4/2010 | Fox |
| 7,726,042 B2 | 6/2010 | Meschan |
| 7,735,351 B2 | 6/2010 | Profit et al. |
| 7,736,272 B2 | 6/2010 | Martens |
| 7,764,990 B2 | 7/2010 | Martikka et al. |
| 7,766,794 B2 | 8/2010 | Oliver et al. |
| 7,775,128 B2 | 8/2010 | Roessingh et al. |
| 7,837,213 B2 | 11/2010 | Colegrove et al. |
| 7,840,346 B2 | 11/2010 | Huhtala et al. |
| 7,841,258 B2 | 11/2010 | Komatsu et al. |
| 7,843,506 B2 | 11/2010 | Ueno et al. |
| 7,845,602 B1 | 12/2010 | Young et al. |
| 7,857,325 B2 | 12/2010 | Copsey et al. |
| 7,872,764 B2 | 1/2011 | Higgins-Luthman et al. |
| 7,874,567 B2 | 1/2011 | Ichida et al. |
| 7,901,292 B1 | 3/2011 | Uhlir et al. |
| 7,909,348 B2 | 3/2011 | Klieber et al. |
| 7,927,253 B2 | 4/2011 | Dibenedetto et al. |
| 7,931,563 B2 | 4/2011 | Shaw et al. |
| 8,016,349 B2 | 9/2011 | Mouri et al. |
| 8,021,270 B2 | 9/2011 | D'Eredita |
| 8,042,427 B2 | 10/2011 | Kawakami et al. |
| 8,045,749 B2 | 10/2011 | Rhoads et al. |
| 8,087,676 B2 | 1/2012 | Mcintyre |
| 8,091,910 B2 | 1/2012 | Hara et al. |
| 8,116,598 B2 | 2/2012 | Filley et al. |
| 8,121,757 B2 | 2/2012 | Song et al. |
| 8,127,900 B2 | 3/2012 | Inoue |
| 8,136,877 B2 | 3/2012 | Walsh et al. |
| 8,141,438 B2 | 3/2012 | Roessingh et al. |
| 8,182,348 B2 | 5/2012 | Uhlir et al. |
| 8,191,964 B2 | 6/2012 | Hsu et al. |
| 8,201,476 B2 | 6/2012 | Tsumiyama |
| 8,210,106 B2 | 7/2012 | Tai et al. |
| 8,221,290 B2 | 7/2012 | Vincent et al. |
| 8,246,065 B1 | 8/2012 | Kodama et al. |
| 8,256,732 B1 | 9/2012 | Young et al. |
| 8,262,100 B2 | 9/2012 | Thomas |
| 8,285,447 B2 | 10/2012 | Bennett et al. |
| 8,286,982 B2 | 10/2012 | Plantet et al. |
| 8,292,274 B2 | 10/2012 | Adoline et al. |
| 8,308,124 B2 | 11/2012 | Hsu |
| 8,317,261 B2 | 11/2012 | Walsh et al. |
| 8,328,454 B2 | 12/2012 | Mcandrews et al. |
| 8,336,683 B2 | 12/2012 | Mcandrews et al. |
| 8,423,244 B2 | 4/2013 | Proemm et al. |
| 8,430,770 B2 | 4/2013 | Dugan et al. |
| 8,457,484 B2 | 6/2013 | Elliott et al. |
| 8,458,080 B2 | 6/2013 | Shirai |
| 8,480,064 B2 | 7/2013 | Talavasek |
| 8,533,746 B2 | 9/2013 | Nolan et al. |
| 8,550,551 B2 | 10/2013 | Shirai |
| 8,596,663 B2 | 12/2013 | Shirai et al. |
| 8,622,180 B2 | 1/2014 | Wootten et al. |
| 8,641,073 B2 | 2/2014 | Lee et al. |
| 8,655,548 B2 | 2/2014 | Ichida et al. |
| 8,727,947 B2 | 5/2014 | Tagliabue |
| 8,744,699 B2 | 6/2014 | Yamaguchi et al. |
| 8,763,770 B2 | 7/2014 | Marking |
| 8,781,680 B2 | 7/2014 | Ichida et al. |
| 8,781,690 B2 | 7/2014 | Hara et al. |
| 8,797,402 B2 | 8/2014 | Said et al. |
| 8,814,109 B2 | 8/2014 | Calendrille et al. |
| 8,833,786 B2 | 9/2014 | Camp et al. |
| 8,838,335 B2 | 9/2014 | Bass et al. |
| 8,845,496 B2 | 9/2014 | Arrasvuori et al. |
| 8,854,499 B2 | 10/2014 | Rothschild |
| 8,868,253 B2 | 10/2014 | Hashimoto et al. |
| 8,888,115 B2 | 11/2014 | Chubbuck et al. |
| 8,936,139 B2 | 1/2015 | Galasso et al. |

(56) References Cited

U.S. PATENT DOCUMENTS

| | | |
|---|---|---|
| 8,950,771 B2 | 2/2015 | Felsl et al. |
| 8,967,343 B2 | 3/2015 | Battlogg et al. |
| 8,972,177 B2 | 3/2015 | Zheng et al. |
| 9,073,592 B2 | 7/2015 | Hsu |
| 9,103,400 B2 | 8/2015 | Becker |
| 9,108,098 B2 | 8/2015 | Galasso et al. |
| 9,126,647 B2 | 9/2015 | Kuo |
| 9,140,325 B2 | 9/2015 | Cox et al. |
| 9,157,523 B2 | 10/2015 | Miki et al. |
| 9,199,690 B2 | 12/2015 | Watarai |
| 9,215,383 B2 | 12/2015 | Milnes et al. |
| 9,229,712 B2 | 1/2016 | Takamoto et al. |
| 9,242,142 B2 | 1/2016 | Vincent et al. |
| 9,278,598 B2 | 3/2016 | Galasso et al. |
| 9,409,052 B2 | 8/2016 | Werner |
| 9,422,018 B2 | 8/2016 | Pelot et al. |
| 9,650,094 B2 | 5/2017 | Laird et al. |
| 9,682,604 B2 | 6/2017 | Cox et al. |
| 10,029,172 B2 | 7/2018 | Galasso et al. |
| 10,082,396 B2 | 9/2018 | Ellis |
| 10,307,644 B2 | 6/2019 | Jones et al. |
| 2001/0014222 A1 | 8/2001 | Honda et al. |
| 2001/0022621 A1 | 9/2001 | Squibbs |
| 2001/0030408 A1 | 10/2001 | Miyoshi et al. |
| 2001/0055373 A1 | 12/2001 | Yamashita |
| 2002/0032508 A1 | 3/2002 | Uchino et al. |
| 2002/0045987 A1 | 4/2002 | Ohata et al. |
| 2002/0047895 A1 | 4/2002 | Bernardo et al. |
| 2002/0050112 A1 | 5/2002 | Koch et al. |
| 2002/0050518 A1 | 5/2002 | Roustaei |
| 2002/0055422 A1 | 5/2002 | Airmet et al. |
| 2002/0089107 A1 | 7/2002 | Koh |
| 2002/0090217 A1 | 7/2002 | Limor et al. |
| 2002/0113347 A1 | 8/2002 | Robbins et al. |
| 2002/0185581 A1 | 12/2002 | Trask et al. |
| 2002/0187867 A1 | 12/2002 | Ichida et al. |
| 2003/0001358 A1 | 1/2003 | Becker et al. |
| 2003/0040348 A1 | 2/2003 | Martens et al. |
| 2003/0054327 A1 | 3/2003 | Evensen et al. |
| 2003/0065430 A1 | 4/2003 | Lu et al. |
| 2003/0128275 A1 | 7/2003 | Maguire |
| 2003/0160369 A1 | 8/2003 | Aplante et al. |
| 2004/0004659 A1 | 1/2004 | Foote et al. |
| 2004/0075350 A1 | 4/2004 | Kuhnel |
| 2004/0091111 A1 | 5/2004 | Levy et al. |
| 2004/0103146 A1 | 5/2004 | Park |
| 2004/0172403 A1 | 9/2004 | Steele et al. |
| 2004/0208687 A1 | 10/2004 | Sicz et al. |
| 2004/0218895 A1 | 11/2004 | Samadani et al. |
| 2004/0220708 A1 | 11/2004 | Owen et al. |
| 2004/0222056 A1 | 11/2004 | Fox |
| 2004/0256778 A1 | 12/2004 | Verriet |
| 2005/0008992 A1 | 1/2005 | Westergaard et al. |
| 2005/0055156 A1 | 3/2005 | Maltagliati et al. |
| 2005/0107216 A1 | 5/2005 | Lee et al. |
| 2005/0110229 A1 | 5/2005 | Kimura et al. |
| 2005/0216186 A1 | 9/2005 | Dorfman et al. |
| 2005/0227798 A1 | 10/2005 | Ichida et al. |
| 2005/0233861 A1 | 10/2005 | Hickman et al. |
| 2005/0239601 A1 | 10/2005 | Thomas |
| 2005/0288154 A1 | 12/2005 | Lee et al. |
| 2006/0026184 A1 | 2/2006 | Hewing et al. |
| 2006/0040793 A1 | 2/2006 | Martens et al. |
| 2006/0064223 A1 | 3/2006 | Voss |
| 2006/0065496 A1 | 3/2006 | Fox |
| 2006/0066074 A1 | 3/2006 | Turner et al. |
| 2006/0111944 A1 | 5/2006 | Sirmans et al. |
| 2006/0136173 A1 | 6/2006 | Case et al. |
| 2006/0163787 A1 | 7/2006 | Munster et al. |
| 2006/0175792 A1 | 8/2006 | Sicz et al. |
| 2006/0176216 A1 | 8/2006 | Hipskind |
| 2006/0185951 A1 | 8/2006 | Tanaka |
| 2006/0213082 A1 | 9/2006 | Meschan |
| 2006/0253210 A1 | 11/2006 | Rosenberg |
| 2006/0289258 A1 | 12/2006 | Fox |
| 2007/0006489 A1 | 1/2007 | Case et al. |
| 2007/0008096 A1 | 1/2007 | Tracy |
| 2007/0011919 A1 | 1/2007 | Case, Jr. |
| 2007/0032981 A1 | 2/2007 | Merkel et al. |
| 2007/0042868 A1 | 2/2007 | Fisher et al. |
| 2007/0070069 A1 | 3/2007 | Samarasekera et al. |
| 2007/0072156 A1 | 3/2007 | Kaufman et al. |
| 2007/0197345 A1 | 8/2007 | Wallace et al. |
| 2007/0199401 A1 | 8/2007 | Kawakami et al. |
| 2007/0213126 A1 | 9/2007 | Deutsch et al. |
| 2007/0239479 A1 | 10/2007 | Arrasvuori et al. |
| 2007/0247306 A1 | 10/2007 | Case |
| 2007/0263981 A1 | 11/2007 | Ueno et al. |
| 2007/0272458 A1 | 11/2007 | Taniguchi et al. |
| 2008/0009275 A1 | 1/2008 | Werner et al. |
| 2008/0009992 A1 | 1/2008 | Izawa et al. |
| 2008/0015089 A1 | 1/2008 | Hurwitz et al. |
| 2008/0018065 A1 | 1/2008 | Hirao et al. |
| 2008/0025561 A1 | 1/2008 | Rhoads et al. |
| 2008/0059025 A1 | 3/2008 | Furuichi et al. |
| 2008/0093820 A1 | 4/2008 | McAndrews |
| 2008/0096726 A1 | 4/2008 | Riley et al. |
| 2008/0099968 A1 | 5/2008 | Schroeder |
| 2008/0109158 A1 | 5/2008 | Huhtala et al. |
| 2008/0116622 A1 | 5/2008 | Fox |
| 2008/0146416 A1 | 6/2008 | Mueller et al. |
| 2008/0163718 A1 | 7/2008 | Chiang |
| 2008/0170130 A1 | 7/2008 | Ollila et al. |
| 2008/0189166 A1 | 8/2008 | Brooks |
| 2008/0200310 A1 | 8/2008 | Tagliabue |
| 2008/0207220 A1 | 8/2008 | Aaron |
| 2008/0254944 A1 | 10/2008 | Muri et al. |
| 2008/0262918 A1 | 10/2008 | Wiener |
| 2008/0303320 A1 | 12/2008 | Schranz et al. |
| 2008/0312799 A1 | 12/2008 | Miglioranza |
| 2009/0048070 A1 | 2/2009 | Vincent et al. |
| 2009/0069972 A1 | 3/2009 | Templeton et al. |
| 2009/0070037 A1 | 3/2009 | Templeton et al. |
| 2009/0098981 A1 | 4/2009 | Del et al. |
| 2009/0118100 A1 | 5/2009 | Oliver et al. |
| 2009/0121398 A1 | 5/2009 | Inoue |
| 2009/0131224 A1 | 5/2009 | Yuen |
| 2009/0192673 A1 | 7/2009 | Song et al. |
| 2009/0233770 A1 | 9/2009 | Vincent et al. |
| 2009/0236807 A1 | 9/2009 | Wootten et al. |
| 2009/0258710 A1 | 10/2009 | Quatrochi et al. |
| 2009/0261542 A1 | 10/2009 | Mcintyre |
| 2009/0277736 A1 | 11/2009 | Mcandrews et al. |
| 2009/0324327 A1 | 12/2009 | Mcandrews et al. |
| 2010/0004097 A1 | 1/2010 | D'Eredita |
| 2010/0004997 A1 | 1/2010 | Mehta et al. |
| 2010/0010709 A1 | 1/2010 | Song |
| 2010/0044975 A1 | 2/2010 | Yablon et al. |
| 2010/0139442 A1 | 6/2010 | Tsumiyama |
| 2010/0160014 A1 | 6/2010 | Galasso et al. |
| 2010/0186836 A1 | 7/2010 | Yoshihiro et al. |
| 2010/0198453 A1 | 8/2010 | Dorogusker et al. |
| 2010/0207351 A1 | 8/2010 | Klieber et al. |
| 2010/0244340 A1 | 9/2010 | Wootten et al. |
| 2010/0252972 A1 | 10/2010 | Cox et al. |
| 2010/0276906 A1 | 11/2010 | Galasso et al. |
| 2010/0292050 A1 | 11/2010 | Dibenedetto et al. |
| 2010/0308628 A1 | 12/2010 | Hsu et al. |
| 2010/0314917 A1 | 12/2010 | Hsieh et al. |
| 2010/0327542 A1 | 12/2010 | Hara et al. |
| 2011/0086686 A1 | 4/2011 | Avent et al. |
| 2011/0095507 A1 | 4/2011 | Plantet et al. |
| 2011/0097139 A1 | 4/2011 | Hsu et al. |
| 2011/0109060 A1 | 5/2011 | Earle et al. |
| 2011/0202236 A1 | 8/2011 | Galasso et al. |
| 2011/0204201 A1 | 8/2011 | Kodama et al. |
| 2011/0257848 A1 | 10/2011 | Shirai |
| 2012/0006949 A1 | 1/2012 | Laird et al. |
| 2012/0007327 A1 | 1/2012 | Talavasek |
| 2012/0080279 A1 | 4/2012 | Galasso et al. |
| 2012/0228906 A1 | 9/2012 | Mcandrews et al. |
| 2012/0253599 A1 | 10/2012 | Shirai |
| 2012/0253600 A1 | 10/2012 | Ichida et al. |
| 2012/0274043 A1 | 11/2012 | Lee et al. |

(56) References Cited

U.S. PATENT DOCUMENTS

| | | |
|---|---|---|
| 2013/0090195 A1 | 4/2013 | Yamaguchi et al. |
| 2013/0119634 A1 | 5/2013 | Camp et al. |
| 2013/0144489 A1 | 6/2013 | Galasso et al. |
| 2013/0221713 A1 | 8/2013 | Pelot et al. |
| 2014/0061419 A1 | 3/2014 | Wehage et al. |
| 2014/0141908 A1 | 5/2014 | Donahoe |
| 2015/0197308 A1 | 7/2015 | Butora et al. |
| 2015/0291248 A1 | 10/2015 | Fukao et al. |
| 2016/0355226 A1 | 12/2016 | Pelot et al. |
| 2017/0106239 A1 | 4/2017 | Sutton et al. |
| 2017/0247072 A1 | 8/2017 | Laird et al. |
| 2017/0282669 A1 | 10/2017 | Cox et al. |
| 2018/0222541 A1 | 8/2018 | Madau et al. |
| 2018/0304149 A1 | 10/2018 | Galasso et al. |
| 2019/0247744 A1 | 8/2019 | Galasso et al. |
| 2020/0357300 A1 | 11/2020 | Galasso et al. |

FOREIGN PATENT DOCUMENTS

| | | |
|---|---|---|
| DE | 3738048 A1 | 5/1989 |
| DE | 69920438 T2 | 10/2004 |
| DE | 10326675 A1 | 12/2004 |
| DE | 102005025811 A1 | 12/2006 |
| DE | 102007063365 A1 | 7/2009 |
| DE | 202008015968 U1 | 4/2010 |
| DE | 202010012738 U1 | 12/2010 |
| EP | 304801 A2 | 3/1989 |
| EP | 552568 A1 | 7/1993 |
| EP | 1138530 A2 | 10/2001 |
| EP | 1188661 A2 | 3/2002 |
| EP | 1241087 A1 | 9/2002 |
| EP | 1355209 A1 | 10/2003 |
| EP | 1394439 A1 | 3/2004 |
| EP | 1449688 A2 | 8/2004 |
| EP | 2103512 A2 | 9/2009 |
| EP | 2357098 A2 | 8/2011 |
| EP | 2479095 A2 | 7/2012 |
| EP | 2357098 B1 | 10/2014 |
| EP | 3216495 A1 | 9/2017 |
| EP | 4039342 A1 | 8/2022 |
| FR | 2432424 A1 | 2/1980 |
| FR | 2952031 A1 | 5/2011 |
| GB | 2465162 A | 5/2010 |
| JP | 57173632 A | 10/1982 |
| JP | 57173632 U | 11/1982 |
| JP | 57182506 A | 11/1982 |
| JP | 01106721 A | 4/1989 |
| JP | 04203540 A | 7/1992 |
| JP | 05149364 A | 6/1993 |
| JP | 2005119548 A | 5/2005 |
| JP | 2007302211 A | 11/2007 |
| JP | 2008238921 A | 10/2008 |
| WO | 9840231 A2 | 9/1998 |
| WO | 99/06231 | 2/1999 |
| WO | 0027658 A1 | 5/2000 |
| WO | 0142809 A2 | 6/2001 |
| WO | 03070546 A1 | 8/2003 |
| WO | 2007017739 A2 | 2/2007 |
| WO | 2007117884 A2 | 10/2007 |
| WO | 2008114445 A1 | 9/2008 |

OTHER PUBLICATIONS

European Search Report for European Application No. 19157965.5, 7 pages, dated Mar. 24, 2020 (dated Mar. 24, 2020).

Smith, ""The Bump Stop" in Engineer to win—Chapter 13: Springs and Shock Absorbers", MBI Publishing Company and Motorbooks, USA XP055430818, ISBN: 978-0-87938-186-8, Dec. 31, 1984, 207.

Fachkunde Fahrradtechnik 4 Auflage, Gressmann_Inhaltv und S, 2011, 206-207.

Statement of Grounds of Appeal, EP App. No. 11153607.4, May 28, 2018, 88 Pages.

European Search Report, European Patent Application No. 14189773.6, dated May 4, 2015, 4 Pages.

EP Search Report for European Application No. 15163428.4, dated Jul. 3, 2017, 7 Pages.

"Communication Re Oral Proceedings for European Application No. 10161906, dated Feb. 15, 2013 (dated Feb. 2, 2015)".

"European Patent Office Final Decision dated Mar. 21, 2013", European Patent Application No. 10161906.2.

"European Search Report for European Application No. 09177128, 4 pages, dated Aug. 25, 2010 (dated Aug. 25, 2010)".

"European Search Report for European Application No. 10161906, 3 pages, dated Sep. 15, 2010 (dated Sep. 15, 2010)".

"European Search Report for European Application No. 11153607, 3 pages, dated Aug. 10, 2012 (Aug. 10, 2012))".

"European Search Report for European Application No. 11172612, 2 pages, dated Oct. 6, 2011 (dated Oct. 6, 2011))".

"European Search Report for European Application No. 12184150, 10 pages, dated Dec. 12, 2017 (dated Dec. 12, 2017)".

"European Search Report for European Application No. 13158034, 4 pages , dated Jun. 28, 2013 (dated Jun. 28, 2013))".

"European Search Report for European Application No. 13189574, 2 pages, dated Feb. 19, 2014 (dated Feb. 19, 2014)".

"European Search Report for European Application No. 15167426 , 4 pages, dated Sep. 18, 2015 (dated Sep. 18, 2015))".

"European Search Report for European Application No. 16167306 , 2 pages, datd Mar. 23, 2017 (dated Mar. 23, 2017)".

"European Search Report for European Application No. 17154191, 2 pages, dated Jun. 28, 2017 (dated Jun. 28, 2017)".

"European Search Report and Written Opinion, European Patent Application No. 13165362.8", dated Sep. 24, 2014, 6 Pages.

"Office Action for European Application No. 13158034.2, 5 pages, dated May 22, 2014".

Nilsson, "Opposition Letter Against EP-2357098", Oct. 13, 2017, 7.

Puhn, "How To Make Your Car Handle", HPBooks, 1981, 7 Pages.

Shiozaki, et al., "SP-861-Vehicle Dynamics and Electronic Controlled Suspensions SAE Technical Paper Series No. 910661", International Congress and Exposition, Detroit, Mich., Feb. 25-Mar. 1, 1991.

European Search Report for European Application No. 21195338.5, 9 pages, dated Jul. 11, 2022.

METHODS AND APPARATUS FOR VIRTUAL COMPETITION

CROSS-REFERENCE TO RELATED APPLICATIONS

This application is a Continuation application of and claims the benefit of co-pending U.S. patent application Ser. No. 16/388,732, filed on Apr. 18, 2019, entitled "METHODS AND APPARATUS FOR VIRTUAL COMPETITION" by Mario Galasso et al., and assigned to the assignee of the present application.

The application Ser. No. 16/388,732 is a Divisional application of and claims the benefit of co-pending U.S. patent application Ser. No. 16/016,444, filed on Jun. 22, 2018, now U.S. Issued U.S. Pat. No. 10,537,790, entitled "METHODS AND APPARATUS FOR VIRTUAL COMPETITION" by Mario Galasso et al. and assigned to the assignee of the present application.

The application Ser. No. 16/016,444 is a Continuation application of and claims the benefit U.S. patent application Ser. No. 14/804,144, filed on Jul. 20, 2015, now U.S. Issued U.S. Pat. No. 10,029,172, entitled "METHODS AND APPARATUS FOR VIRTUAL COMPETITION" by Mario Galasso et al. and assigned to the assignee of the present application.

The application Ser. No. 14/804,144 is a Continuation application of and claims the benefit of U.S. patent application Ser. No. 12/626,384 filed on Nov. 25, 2009, now U.S. Issued U.S. Pat. No. 9,108,098 entitled "METHODS AND APPARATUS FOR VIRTUAL COMPETITION" by Mario Galasso et al. and assigned to the assignee of the present application.

The application Ser. No. 12/626,384 claims priority to and benefit of U.S. provisional patent application 61/117,608 filed Nov. 25, 2008, entitled "METHODS AND APPARATUS FOR VIRTUAL COMPETITION" by Mario Galasso et al., which is incorporated herein, in its entirety, by reference.

FIELD OF THE INVENTION

Embodiments of the invention generally relate to methods and apparatus for facilitating virtual contests of speed and performance. Particular embodiments of the invention relate to methods and apparatus for monitoring and storing a global position with time and submitting results to a central location such as an internet site (digitally readable medium using, for example, electromagnetic signals, or specifically electrical or optical signals).

BACKGROUND

Cross country mountain bike racing has become irrelevant to the broad cross section of mountain bike enthusiasts. Cross Country racing, due to its Olympic association, has become little more than road racing in the dirt. Due to Olympic aspirations, even local and regional amateur off-road races have become less and less technical and are often navigable with little or no suspension. Off-road gravity racing (downhill racing—usually point-to-point) is popular with the new and younger mountain bikers entering the sport. However, because specific venues are needed for proper gravity racing such as downhill racing, 4 cross and dual slalom, extensive travel can be required of the would be racer.

A large majority of mountain bike enthusiasts ride full suspension bikes of 4-6" of travel. They typically enjoy "all mountain" riding for both the climbing and fitness aspects of the sport as well as the descending and adrenaline fed aspects of the sport. Ride types vary by region as terrain varies. In most cases, favorite local rides include terrain that challenges all of a mountain biker's skills.

Because cross country racing formats have diverged from mainstream interests and because sanctioned downhill racing venues are relatively few and far between, many riders prefer riding in their own local areas. Such local rides are usually a close car ride away and in some cases are able to be accessed by the rider with only their mountain bike, thereby requiring no motor vehicle transportation at all. For the younger downhill riders, it has become common place to develop trails with easy motor vehicle access for shuttling back to the top after the decent. Some of these gravity oriented trails are as challenging as the world or regional class courses the riders would otherwise have to travel many hours to compete on (were they to compete in world or regional class events). In all of these local riding scenarios, the competition is typically amongst the locals who create the trails and/or ride them. What is needed is a mountain bike racing format that makes racing relevant again, both locally and to the world, and to engage the enthusiast who currently chooses to stay local and ride local.

SUMMARY

In one embodiment of the present technology, a system configured to be coupled with a participant of an activity comprises: a participant activity monitoring unit configured for monitoring a performance of the activity by the participant; an activity information module configured for storing performance information corresponding to the activity; and a participant performance correlator configured for delivering comparative performance data based on the monitored performance of the activity by the participant and the stored performance information. In one embodiment, the system further comprises a feedback module configured for providing information to the participant based on said comparative performance data, wherein the feedback module comprises a visual cue generator and/or an audio cue generator.

In one embodiment of the present technology, a computer usable storage medium comprising instructions that when executed by a computer cause the computer to perform a method for performance comparison of multiple performances of an activity, the method comprises: receiving data associated with one or more monitored performances of an activity; storing performance information corresponding to the activity; and providing comparative performance data to a participant based on the received data associated with the one or more monitored performances and the stored performance information. In embodiment, the one or more monitored performances are performed by a single participant and/or a plurality of participants. In one embodiment, the storing performance information corresponding to the activity comprises storing shock absorption information, cadence information, velocity information, gear positioning information, suspension information, and/or the heart rate of the participant. In one embodiment, the storage medium comprises a link to a network. In one embodiment, the network comprises an internet. In another embodiment, performance feedback is provided to a user while the user is reviewing the activity.

In one embodiment of the present technology, a method for enhancing revenue generation comprises: receiving at a computer user activity information corresponding to a performance of an activity; analyzing the user activity information at the computer; and based on the analyzing, generating at the computer feedback for use by a user, the feedback corresponding to improved performance of the activity. In one embodiment, the feedback is provided to a device local to the user for promulgation to the user. In another embodiment, a recommendation for a component selection and/or component operation for improved performance of the activity is generated. In one embodiment, the feedback is generated while the user is participating in the activity. This feedback may be a voice of a person of interest to the participant. Additionally, the feedback may be generated through visual and/or audio cues.

In one embodiment of the present technology, a method for virtually competing comprises: recording performance information corresponding to a performance of the activity; storing the performance information to a memory; and submitting at least a portion of the stored performance information to a networked digitally readable medium such that the stored performance information is available for use by the participants of the activity. In one embodiment, the recording of the performance information corresponding to a performance of the activity is repeated for different performances of the activity. In another embodiment, the recording of the performance information corresponding to a performance of the activity is performed by different participants of the activity. In one embodiment, the networked digitally readable medium generates a rating for the performance of the activity compared to other submitted performances of the activity, determines a winner of the submitted performances of the activity, and/or provides recommendations regarding the appropriate component selection for improved performance of the activity. In one embodiment, the networked digitally readable medium stores performance information corresponding to one or more of the following: shock absorption; cadence; velocity; gear positioning; suspension; participant's heart rate; power; time; breaking; cornering speed; and calories burned.

In one embodiment of the present technology, a computer usable storage medium comprising instructions that when executed by a computer cause the computer to perform a method for recreating a performance of an activity from a camera perspective, the method comprises: receiving a video feed associated with one or more monitored performances of an activity; receiving data associated with the one or more monitored performances; storing performance information corresponding to the activity; correlating the video feed with the data; and based on the correlating, generating a real time recreation of a performance of the activity from a camera perspective. In one embodiment, the one or more monitored performances are performed by a single participant and/or a plurality of participants. In one embodiment, the providing of comparative performance data to a participant based on the received data associated with the one or more monitored performances and the stored performance information forms a basis of a virtual race competition. This providing of comparative performance data, in one embodiment comprises rating the one or more monitored performances and/or selecting a winner of the one or more monitored performances. In one embodiment, the providing of comparative performance data to a participant based on the received data associated with the one or more monitored performances and the stored performance information comprises providing a recommendation corresponding to an improved performance of the activity. The providing of a recommendation corresponding to the improved performance of the activity may comprise generating a recommendation for an appropriate component selection for the improved performance of the activity and/or generating a recommendation for a component operation for the improved performance of the activity. In one embodiment, the providing of comparative performance data to a participant based on the received data associated with the one or more monitored performances and the stored performance information comprises: providing feedback to a user comprising a voice of a person of interest to the participant, generating feedback to a user through visual cues, and/or generating feedback to a user through audio cues. In one embodiment, the storing performance information corresponding to the activity comprises storing shock absorption information, cadence information, velocity information, gear positioning information, suspension information and information regarding a heart rate of the participant. In one embodiment, one or more downloadable participatory activities is provided.

In one embodiment of the present technology, a system for providing data to a participant in an activity, which activity involves the participant moving along a predefined geographical route, comprises: a server storing a plurality of predefined geographical routes, each predefined geographical route comprising a plurality of geographical markers distributed along the route, and each geographical marker having data associated therewith, such as audio, video, image and/or text data; and a device to be taken with the participant during the activity, which device comprises a network interface for connecting to the server, a geographical location interface, and a memory storing computer executable instructions that when executed enable the device to: connect to the server prior to or during the activity and download and store in the memory at least one of the predefined geographical routes, the geographical markers and the data associated therewith; and monitor its current geographical position during the activity to determine if and when the device is at or near to one of the geographical markers, and if so, to output to the participant the data associated with that geographical marker. In one embodiment, the device further comprises a wireless interface and a hands-free headset or earpiece to be worn by the participant, the arrangement being such that, in use, during step the monitoring of its current geographical position during the activity to determine if and when the device is at or near to one of the geographical markers, and if so, to output to the participant the data associated with that geographical marker, the data is sent as audio data through the wireless interface addressed to the hands-free headset whereby the participant is able hear instructions and/or information relating to the activity in order to reduce distraction. In one embodiment, the device is sized and adapted to be hand-held by the participant, or mounted on an apparatus being used by the participant during the activity. In one embodiment, the device further comprises an interface for receiving performance data from the one or more performance monitoring device associated with the participant during the activity, and which computer-executable instructions cause the device to compare the performance data with pre-stored performance data upon determination in step of monitoring of its current geographical position during the activity to determine if and when the device is at or near to one of the geographical markers, and if so, to output to the participant the data associated with that geographical marker, that the device is at or near one of the geographical markers, and to provide an output to the participant based on the comparison. In one embodiment, the device comprises a network interface for connecting to a remote server, a geographical location interface, and a memory storing computer executable instructions that when executed enable the device to: connect to the server prior to an activity and download and store in the memory at least one of the predefined geographical routes, the geographical markers and the data associated therewith; and monitor its current geographical position during the activity to determine if and when the device is at or near to one of the geographical markers, and if so, to output to the participant the data associated with that geographical marker. In one embodiment, the server for use in the system comprises: a memory storing a plurality of predefined geographical routes, each predefined geographical route comprising a plurality of geographical markers distributed along the route, and each geographical marker having data associated therewith, such as audio, video, image and/or text data; and a network interface to which, in use, remote devices may connect to the server and download one or more of the predefined geographical routes and the geographical markers and data associated therewith.

In one embodiment of the present technology, a computer for processing user-generated content, which content comprises two parts: video data of a participant's perspective during performance of an activity such as a sporting activity, and geographical position data of the participant during that performance; which computer comprises: a network interface for receiving said user-generated content; a processor; and a memory storing computer-executable instructions that when executed cause the processor to correlate the video data with the geographical position data, and to store as a data pack locally on the computer or remotely on a server the content and a relationship between its two parts, whereby upon playback of the video data, position-related data may be displayed alongside the video data, which position-related data is displayed according to the participant's geographical position in the video data during playback. Moreover, in one embodiment, the computer-executable instructions further cause the processor to associate the data pack with a local, national or global map database, in which association a mapping is stored between the data pack and a geographical position at which the activity took place, whereby a third party having access to the computer may browse and search the map database by geographical position and retrieve one or more data packs associated with that geographical position. In one embodiment, the computer executable instructions further cause the processor to augment the video data with simulated video data generated from the map database. In another embodiment, the computer executable instructions further cause the processor to take one data pack and to search the map database for other data packs comprising geographical position data which matches at least one point or part of the geographical position data of the one data pack, and to generate a new data pack comprising new video data of a new route not already stored in the map database, which new video data comprises a respective section of video data from at least two other data packs which have been edited together to provide a video of the new route.

In one embodiment of the present technology, a computer-implemented sports device that is wearable or otherwise transportable by a participant during a sports activity comprises: an interface for receiving data from one or more performance monitoring device associated with the participant during the activity; a visual display for displaying performance-related data to the participant; and a memory storing computer-executable instructions for controlling the sports device and a processor for processing the performance-related data; wherein, at least periodically during use, the majority of a display area of the visual display is used to display a non-numeric indication of one of the performance-related data. In one embodiment, a sports device as claimed in claim 1, wherein the non-numeric indication comprises one color of at least two different colors selectable by the sports device.

In one embodiment of the present technology, a video recording apparatus comprises: a aperture for directing optical wavelengths; an optical to digital transducer in a path of the wavelengths; a wireless receiver having communication protocol instructions; an antenna connected to the wireless receiver; a memory having correlation instructions for correlating data received by the receiver with digital output from the optical to digital transducer; and a processor for running the correlation instructions.

BRIEF DESCRIPTION OF THE DRAWINGS

The accompanying drawings, which are incorporated in and form a part of this specification, illustrate embodiments of the present technology for methods and an apparatus for a virtual competition, together with the description, serve to explain principles discussed below.

DESCRIPTION OF EMBODIMENTS

Reference will now be made in detail to embodiments of the present technology, examples of which are illustrated in the accompanying drawings. While the present technology will be described in conjunction with various embodiment(s), it will be understood that they are not intended to limit the present technology to these embodiments. On the contrary, the present technology is intended to cover alternatives, modifications and equivalents, which may be included within the spirit and scope of the invention as defined by the appended claims.

Furthermore, in the following detailed description, numerous specific details are set forth in order to provide a thorough understanding of embodiments of the present technology. However, embodiments of the present technology may be practiced without these specific details. In other instances, well known methods, procedures, components, and circuits have not been described in detail as not to unnecessarily obscure aspects of the present embodiments.

Unless specifically stated otherwise as apparent from the following discussions, it is appreciated that throughout the present detailed description, discussions utilizing terms such as "receiving", "storing", "providing", "rating", "analyzing", "generating", "recording", "submitting", "correlating", "presenting", "selecting", "corresponding", or the like, refer to the actions and processes of a computer system, or similar computing device (e.g. electronic). The computer system or similar electronic computing device manipulates and transforms data represented as physical (electronic) quantities within the computer system's registers and memories into other data similarly represented as physical quantities within the computer system memories or registers or other such information storage, transmission, or display devices. Embodiments of the present technology are also well suited to the use of other computer systems such as, for example, optical and mechanical computers.

Overview

Embodiments of the present technology provide an interactive race system and method that will empower the local enthusiasts to race and compete, non-concurrently if desired, on their favorite local trails without the hassle of long travel, early morning registration times, limited course time, undue expense, crowded courses, governing body intrusions, and others setting the courses on which to compete. Embodiments of the present technology provide a system and method empowering race enthusiasts to race and compete, non-concurrently, on world class race courses and against professional athletes on those courses.

Figure 1:
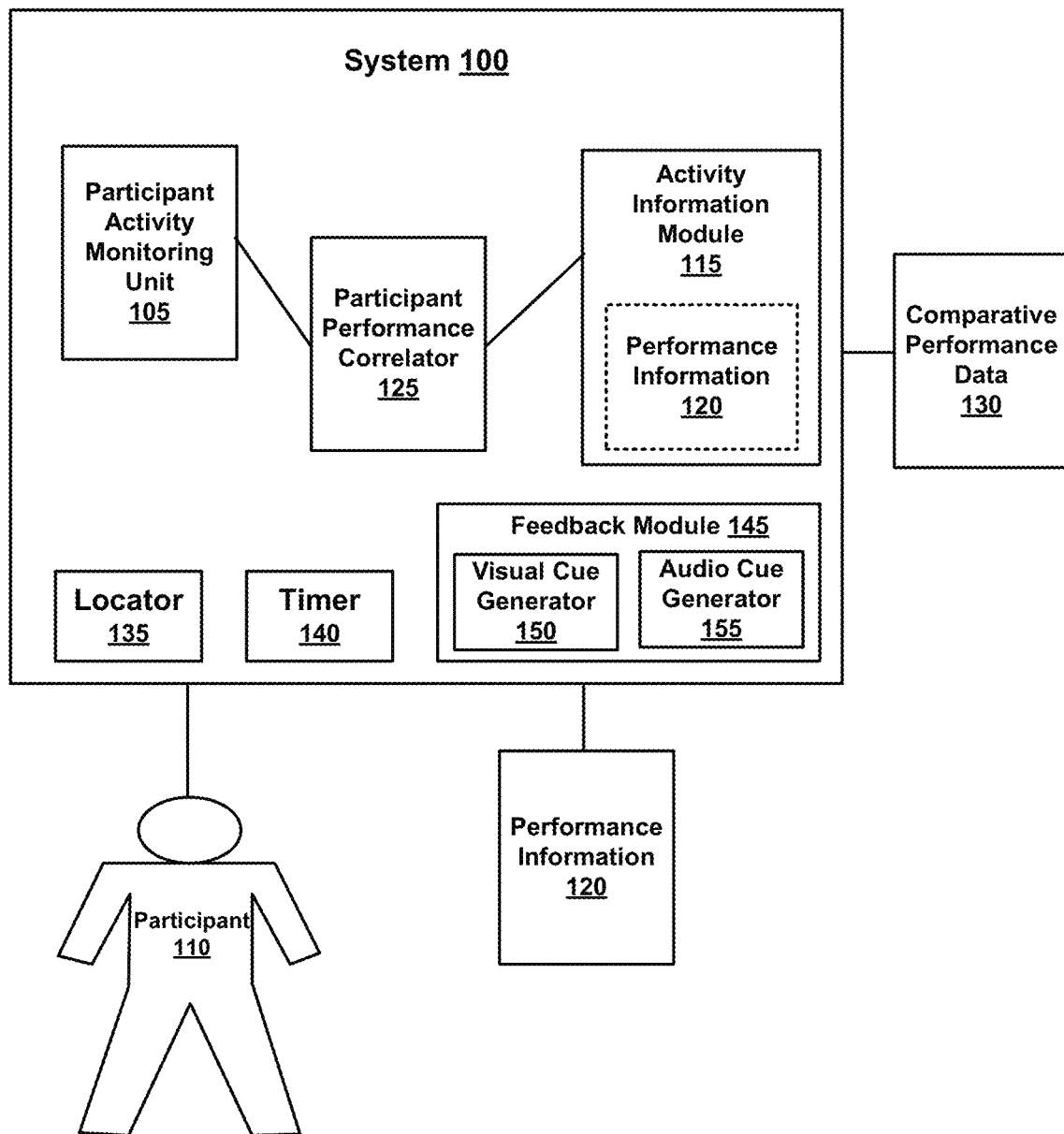
FIG. 1 is a block diagram of a system 100 configured to be coupled with a participant of an activity as disclosed herein.

In general, embodiments hereof pertain to a system for delivering performance data regarding a participant's performance, or anticipated performance, of an activity. The system 100 of FIG. 1 is configured to be coupled with the participant and/or participant's vehicle. A participant activity monitoring unit monitors the participant's performance of an activity. For example, the participant's location, speed and power output may be monitored. Additionally, an activity information module stores information corresponding to or related to the participant's performance of the activity. For example, the activity information module may store data associated with a professional's performance of the same activity. Then, based on the participant's monitored performance and the stored professional's performance data, a participant performance correlator delivers comparative performance data to the participant. In one instance, this comparative performance data may come in the form of advice to the participant while performing the activity. Additionally, the data may include a rider's time or distance behind or ahead of a professional's [recorded] performance at any point on the course.

More particularly, and using an example of a mountain biker traversing a trail that has been catalogued in accordance herewith, embodiments hereof enable the mountain biker to receive pre-recorded audible advice during his ride, via for example a wireless ear piece or "bud," to improve his speed and/or technique over the trail. In one embodiment, system 100 is coupled with the mountain biker. More specifically, system 100 may be attached to the mountain biker's bike. In one embodiment the system 100 communicates with and receives data from, via wire or wireless (e.g. Bluetooth protocol, AGENT WITH TRAINING CENTER [ANT] by Garmin of George Town, Cayman Islands) components of the bicycle such as suspension performance sensors, power sensors (e.g. POWERTAP HUB by Saris Cycling Group, Inc. of Madison Wisconsin, United States, U.S. Pat. No. 5,031,455 incorporated in its entirety herein by reference) speed sensors, accelerometers, strain gages, and other suitable telemetry devices. System 100 has stored thereon information regarding the trail as well as the performance data of a professional rider having traversed the same trail. Such data may be downloaded, in advance of a chosen ride, from a remote server, such as is located on the internet, by connecting system 100 to a network and accessing a selected network address containing pre-recorded ride information catalogued by ride location (e.g. by selectable icon located proximate the recorded trail on a map promulgated by GOOGLE EARTH of Google of Mountain View, California, United States) and downloading ride information associated with the chosen ride. As the mountain biker rides over his chosen trail, system 100 monitors parameters of the mountain biker and bike, such as global location, speed, operating gear ratio, suspension usage, power output, etc. System 100 may monitor any or all of the mountain biker's speed, global position, elevation, distance traveled, power output and heart rate. System 100 may take measurements of any or all selected parameters at a user selected frequency or frequencies. Optionally, system 100 may calculate a rate of change of a given parameter and adjust a measurement and recording (sampling rate) frequency in response to the calculated rate of change. In one embodiment, system 100 increases measurement and recording frequency of a given parameter in response and proportion to a higher rate of change of that given parameter. Such increased frequency affords the increased data resolution required to represent the characteristic behavior of a parameter. In one embodiment, the system includes a video camera for recording real time rider perspective and an audio recorder for recording real time rider impressions. All of the data recorded by system 100 is cross-correlated so that a given ride may be broken down incrementally with full data sets attributable to each increment. In one embodiment, increments correspond to sampling rate for a given data set such that incremental differences vary depending on the data set chosen for increment basis. In other words, for example, increments for elevation will each include a complete data set but the difference between recorded data points will be dictated by the frequency at which elevation was recorded. Further to the example, a different data perspective may be had, viewing the same data set from the perspective of a global position, where the global position data was changing at a different rate than elevation. The data set for the global position will be complete for each "bread crumb" associated with that database. Additionally, each data point of elevation will also represent a complete data set. As such, the raw data for any data type may be in excess of the chosen increment for that data type.

In one embodiment, system 100 compares the mountain biker's progress with that of the professional rider's progress through the trail. Based on this comparison, system 100 is able to offer advice to the mountain biker during his trail ride. The advice is pre-recorded by a previous rider of the trail or trail segment and is triggered to be delivered to the current rider by system 100 based on the occurrence of a data input trigger in real time. For example, system 100 may warn the mountain biker of an approaching small steep hill and advise that the mountain biker should be prepared to shift into a lower gear and to increase his pedaling RPMs. Such a warning would be triggered by a GPS real time input that such a "steep hill" was upcoming. The GPS real time input would be derived from real time GPS data as compared, by system 100, to the previously downloaded GPS data (and location in advance of the steep hill) that gave rise to the advice during the recording run by the professional or other pre-recording rider. Other useful information that can be correlated with actual trail position and elevation and delivered to the rider in advance includes but is not limited to: braking requirements; upcoming cornering events; jumps drop and offs; and natural obstructions such as rocks and logs. In one embodiment, the rider's physical parameters, including power output, are monitored and audio advice may include, but is not limited to: slow down; take an electrolyte supplement; and drink liquid. Such physiological advice may also be given in response to a global location based on previously recorded rider experience. Such advise may be given in response to data from, for example, a power meter. In that event, a rider's maximum sustainable output wattage (or heart rate) may be known and when such amount is exceeded, the rider may be prompted to slow down. In one embodiment, a rider may be instructed to slow down because a lower percentage of the rider's maximum wattage is required as a cap at a preliminary phase of the ride (in other words, system 100 "knows" what the rider must yet traverse and has calculated a power spread for the rider over the course and is warning the rider that the power output allotment for a given course section is being exceeded). In one embodiment, this advice may be given in the professional rider's voice via an ear bud (wired or wireless) or similar audio transmitter interfaced as an output with the system 100. In one embodiment, the advise may be displayed on a user display such as an LCD screen. In one embodiment, some or all of the advice may take the form of warning and go lights, associated with a display or device on the bike, such as, for example: a green light for proper RPM or speed in a given section; and a red light for too low an RPM or speed. If the rider is engaged in real time virtual competition with a previously recorded rider (or fabricated goal) goal performance ("chasing a rabbit"), a green light may indicate that the rider is even with or ahead of the goal and a red light may indicate that the rider is behind the goal. In one embodiment the rider may choose the red light green light thresholds. For example, the rider may choose for a green light to show only if the rider is 10% faster than the performance goal being used. The "rabbit" performance is previously downloaded, with or without advice, and the rider's system 100 GPS tracks the current ride in comparison to the pre-designated or recorded "rabbit" ride. In this manner, the mountain biker may feel as if he has received the best possible instructions and/or competition to improve his ride and from a professional whom he admires.

Additionally, embodiments of the present technology enable a participant's recorded performance of an activity to be uploaded to a website. At this website, the participant's performance may be compared to other performances of the same activity by the participant or by other participants. Based on these comparisons, advice may then be given to the participant via the website regarding ways to improve his performance of that activity. In one embodiment, riders may upload their performances over a given track or trail and view comparisons of their data with other riders' data sets. Such comparative data may be viewed graphically. Such data may be viewed incrementally so that varying comparative performance are apparent at different, for example, locations of the track. The data may be used to generate a virtual "race" using post run results for all contestants but showing contestants' results incrementally in "real race time" as generated from the compared data sets. In other words, the contestant riders may view, on a 3D trail map or split screen with actual video or incremental and changing parameter data, a race between the recorded run results (i.e. the contestants). In one embodiment, a website may host a virtual race over a given period of time. For example, a race may be open for a month. During such month all certified race results are posted to the website. Results may be certified by encryption key stamped GPS encoded data or other comparable method where a rider checks in with the website, receives a download data key for attachment to a trail run file (where the key is activated for one time use by the rider and associated with a time stamped data run), activates the key prior to the run and ends the run directly after the ride (run), thereby certifying the GPS correlated run data with the upload race key. At the end of the open period (e.g. month) race results are posted by categories selected by the website (e.g. age, gender, trail, bicycle type) and winners announced. The website will include algorithms for comparing GPS data to ensure that contestants in a given race all rode substantially the same course. Such algorithm can further check for large speed anomalies that may indicate non-conforming rider behavior (e.g. motor racing when bicycle was the call).

In another example, a skier races down a slalom ski run, swerving around five gates. System 100 monitors and records the skier's performance in relation to any or all relevant parameters. In one embodiment, a parameter comprises beacons associated with geographic features, such as for example, the slalom gates and the system 100 includes a transponder for timing passages relative to such gates. In one embodiment, the system 100 includes a radio frequency identification tag (RFID) that records gate passage signals in the system 100. In one embodiment, the gate passage signals are correlated with time. In one embodiment, the RFID tag is passive and a discreet RFID tag may be associated with each individual user. In one embodiment, the skier may receive advice directly, via audio and/or visual interface, from system 100 as to how fast to approach and how wide to turn around each gate. In one embodiment, the gate beacon or beacons may transmit advice data to the system 100 in real time and the skier may receive audio, visual or tactile input from the system 100 in response to the gate beacon transmission. In one embodiment, the gate beacons process data and generate transmissions to the skier (via system 100) based on real time interaction with the internet. In one embodiment, physiological parameters of the skier and physical parameters of the ski (e.g. heart rate and ski flex respectively) are measured by sensors and factor into the advice given at various points on the course or run.

In one embodiment, the skier may upload his recorded performance data (stored in system 100 during run time) to a website configured for receiving this information, and compare his completed ski run to his previous ski runs or to other skiers' performances. The website may deliver advice to the skier, via computer interface, cell phone interface, or other suitable internet user interface, to improve the skier's performance. This advice may come in the form of technique advice and/or equipment selection, tuning and/or replacement. For example, a skier may be advised to change up his skis for a shorter pair, a more technically advanced pair, or a newer model that would be more appropriate for a particular ski run. Additionally, in another embodiment, the website may rate various skiers' performances over the ski run and select a winner.

Thus, embodiments of the present technology enable a virtual competition, within which a participant may participate on his own time, while still being able to compare his incremental and overall results and data with a larger groups' and other users. Furthermore, embodiments enable a participant of an activity to receive high quality advice from a professional, experienced in the particular run or condition, during the performance of that activity. In one embodiment, general conditions are experienced by professionals, such as, for example deep powder snow skiing, and a recording of advice or advisory signals are transmitted to system 100 when appropriate conditions occur in real time. For example, a skier may be out during a heavy snowfall while using system 100 that is tuned into an appropriate web connection or local beacon for receiving real time mountain or weather conditions. System 100 may determine its location, and real web or beacon information correlated with that location may be transmitted to the skier advising the skier of the heavy snow cover or snow fall conditions and making recommendations associated therewith (even associated therewith in relation to a given ski run which the skier is traversing or comprising a warning such as "get off the mountain and seek shelter"). Moreover, embodiments recommend equipment replacement and upgrades to participants, based on their performances, to help improve the participant's overall performance, thereby enhancing revenue generation for the maker and/or seller of the equipment. In one embodiment, equipment or service providers in a given sport may pay for, and web hosts may sell, space (virtual web site space) for posting data and information that are useful to trail users so that the providers advertising information may be transmitted therewith. As mentioned previously, tuning characteristics for mountain bike suspension and advice pertaining thereto may be broadcast to a rider of a particular run or trail. In one embodiment, a user may key in a chosen catalogued run or trail or portion thereof and receive advice in advance of executing the run or trail.

Example Architecture of System 100

One embodiment of the present technology comprises a hosted and administered competition website designed to accept information from and integrate with commercially available Global Navigation Satellite System (GNSS) technology. Referring now to system 100 of FIG. 1, one embodiment comprises a participant activity monitoring unit 105 for monitoring a performance of an activity being performed by a participant, an activity information module 115 for storing performance information corresponding to the activity and a participant performance correlator 125 for delivering comparative performance data based on the monitored performance of the activity by the participant and the stored performance information. For example, the participant activity monitoring unit 105 may determine the geographic position of system 100 while an activity is being performed For the purposes of embodiments of the present technology, the term "geographic position" means the determining in at least two dimensions (e.g., latitude and longitude) the location of system 100. In one embodiment of the present technology, participant activity monitoring unit 105 is a satellite based position determining system and receives navigation data from satellites via an antenna (not shown). In one embodiment, the antenna is remote from the participant activity monitoring unit 105 ("PAMU 105") and communicates therewith via a local wired or wireless preferably low power protocol. Such a remote antenna facilitates communication with satellites in the event that the actual PAMU 105 is out of clear satellite view. In use, such a remote antenna may be placed on the participant or vehicle at a location that more often has a more clear satellite view than the PAMU 105. In one embodiment, an antenna/local beacon, that communicates with the PAMU 105, may be placed on a hill top or other area, having a clear satellite view, proximate a trail or track to be ridden. In one embodiment, three spaced antenna/local beacons may be used and the PAMU 105 includes a position differentiator for triangulating from the local antenna/beacons and combining such data with satellite data from one or more of the antenna/beacons to establish a net global position calculation set for the trail run. Examples of satellite based position determining systems include the global positioning system (GPS) navigation system, a differential GPS system, a real-time kinematics (RTK) system, a networked RTK system, etc. . . .

It should be appreciated that embodiments of the present technology are also well suited for using other position determining systems, such as for example, cell tower triangulation, as well as ground-based position determining systems, or other satellite-based position determining systems such as the Global Navigation Satellite System (GNSS), the Global Orbiting Navigation Satellite System (GLONASS), Compass/Beidu, or the Galileo system currently under development.

Additionally, system 100 may be well suited to utilize a variety of terrestrial-based and satellite-based position determining systems. For example, terrestrial based broadcast signals such as LORAN-C, Decca, and radio frequency beacons may be utilized.

While examples herein refer to an "activity" as mountain bike courses and virtual interactive competition, the disclosure hereof is equally suited for use to facilitate a wide variety of competitive events/activities such as, but not limited to, running, swimming, motor vehicle sports, boating (e.g., sailing), rock climbing, mountain climbing and any other suitable competitive sport comprising either point to point or closed loop type competition or combinations thereof. The disclosure herein is also suitable to facilitate time/location finding events/activities such as, but not limited to, rally racing, enduro racing and orienteering, or in other words, a virtual racing and competition (VCR).

Referring still to FIG. 1, in one embodiment PAMU 105 is coupled with a locator 135 and/or a timer 140. The locator 135 determines the location of the participant 110 during an activity. The timer 140 monitors a time of a location of the participant 110 during an activity.

In another embodiment, activity information module 115 stores performance information corresponding to the activity that is being performed and which is being monitored by participant activity monitoring unit 105. Performance information 120 is information that is related to the activity that is being monitored by the participant activity monitoring unit 105. For example, if the activity is a mountain bike trail ride, then the performance information 120 that is stored in system 100's activity information module 115 may be, but is not limited to, information relating to shocks (e.g. spring rate, damping rate, pressure, travel velocity, pressure differential, force, displacement), cadence, velocity, gear positioning, athlete power output, suspension, and the heart rate of the participant. In one embodiment, such performance data enters the data storage set as correlated with global position and time and other data on an incremental basis so that analysis may be performed incrementally stepwise through the run. Further, the performance information 120 may also be one or more prior performances of the activity by the participant 110 and/or someone else. Information recorded from the prior performances may also include course layout registration for local, regional, national, and global courses, and provides the timing system for competitors on registered courses. Additionally, performance information 120 may also be stored instructions relating to the activity. Of these stored instructions, selected instructions may be delivered to the participant 110 (e.g. audibly, visually, tactilely), based on the participant 110's monitored performance of the activity. All of the foregoing data types and instruction types may be stored incrementally for analysis or delivery at chosen increments (e.g. time, location, gear position—increments of a chosen baseline data type).

Embodiments of the present technology may include a feedback module 145. In one embodiment, the feedback module 145 includes a visual cue generator 150. In yet another embodiment, the feedback module 145 includes an audio cue generator 155. A visual cue generator 150 provides a visual cue to the participant 110, such as but not limited to, a flashing light, a colored light, a series of colored lights, etc. . . . . . The audio cue generator 155 provides an audio cue to the participant 110, such as but not limited to, a siren, a beep, a series of beeps, a voice, multiple voices, etc. . . .

Figure 2:
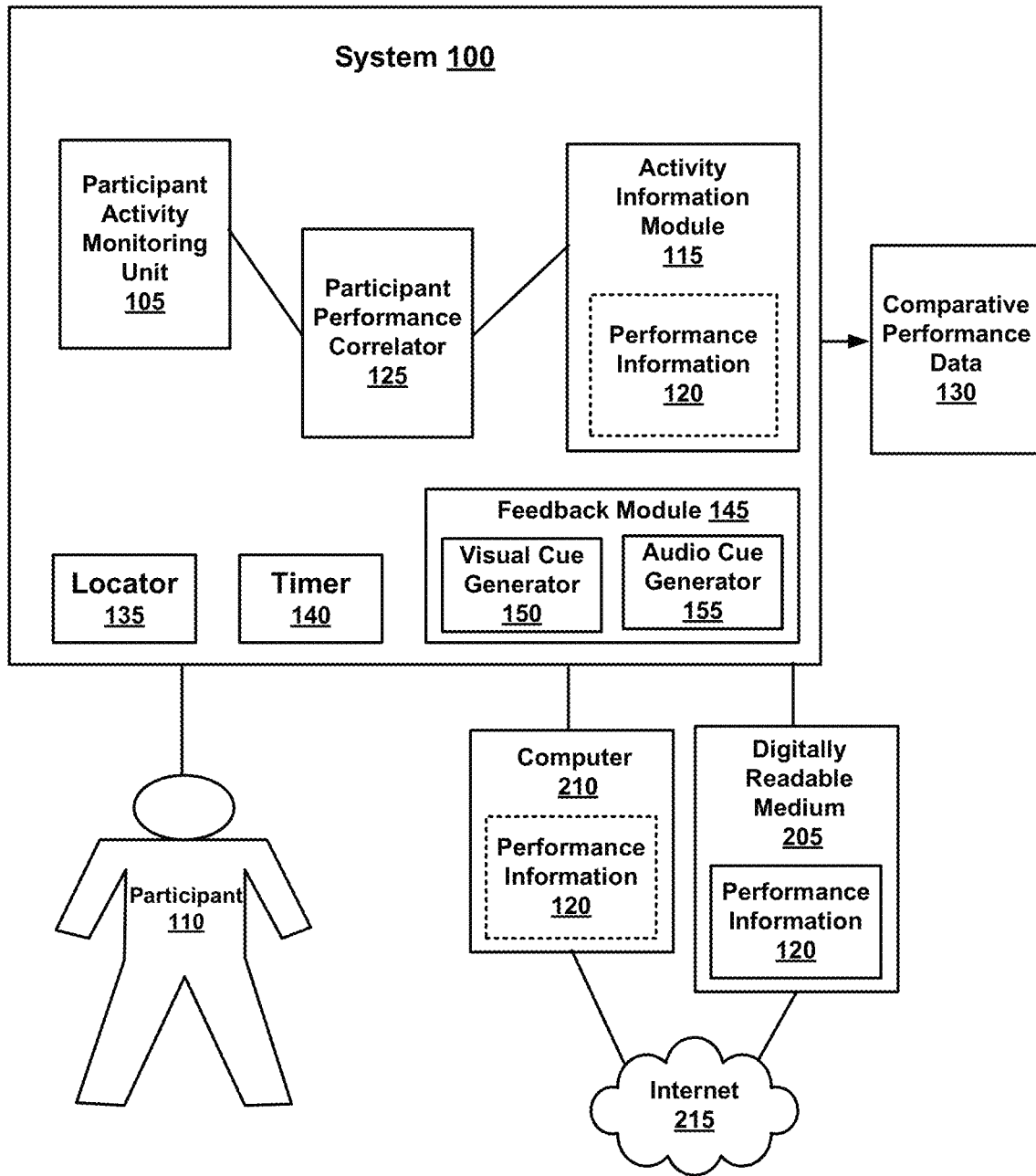
FIG. 2 is a block diagram of a system 100 configured to be coupled with a participant of an activity as disclosed herein.

Referring now to system 100 of FIG. 2, in one embodiment, system 100 may be coupled with a computer 210, wired and/or wirelessly. In another embodiment, system 100 may be coupled with a digitally readable medium 205, wired and/or wirelessly. The computer 210 may access the digitally readable medium 205 via the internet 215, and vice versa.

The digitally readable medium 205, such as for example a server with a memory device, provides course layout registration for local, regional, national, and global courses, and provides the timing system for competitors on registered courses.

In one embodiment, cycling computers such as, but not limited to, those sold under the trademark EDGE 605 and EDGE 705 by Garmin of George Town, Cayman Islands with a GNSS capability may be utilized to provide traces of proposed competition courses. These cycling computers are also used for providing timing for the courses on which a participant wants to compete. In one embodiment, GPS equipped cell phones such as the IPHONE by Apple, Inc. of Cupertino, California, United States, may be used to gather GPS and other data and, with properly written application programming, to function substantially as an embodiment of system 100 (including audio instruction output and ear bud interface). In one embodiment, local groups or individuals can contact the VRC administrators to have a course registered as an authorized and supported competition venue. In another embodiment, a competition venue will have criteria for registering a course. The option of registering a course will be for legal trails only. In one embodiment, a course may not have any speed limit thereon. A GNSS trace of the course may be submitted, including registering start and finish points. This course may be a point to point or a closed course loop. In one embodiment, such as for example, auto rally, orienteering or moto-enduro, a course may have speed limits through various legs (between check points) and the system 100 is used to verify compliance such that the rally style race may be run in non-concurrent space as described herein referring to other racing such as mountain bike racing. In one embodiment, there may be a low canopy coverage for a solid GNSS signal.

Thus, embodiments of the present technology provide a system for comparing the performance of an activity by a participant with the stored performance information corresponding to the activity. Based on this comparison, comparative performance data is delivered to the participant and/or one other than the participant. Based on this performance comparison, a participant may then receive feedback during or after the performance of the activity. This feedback may take the form of visual and/or audio cues.

Example Operation of System 100

More generally, in embodiments in accordance with the present technology, system 100 is utilized to provide comparative performance data 130. More particularly and referring now to 300 of FIGS. 3a and 3b, a flowchart of a method for performance comparison of multiple performances of an activity is shown. In one embodiment, process 300 is carried out by processors and electrical components under the control of computer readable and computer executable instructions. The computer readable and computer executable instructions reside, for example, in data storage features such as computer usable volatile and non-volatile memory. However, the computer readable and computer executable instructions may reside in any type of computer readable medium. In one embodiment, process 300 is performed by system 100 of FIG. 1.

Figure 3A:
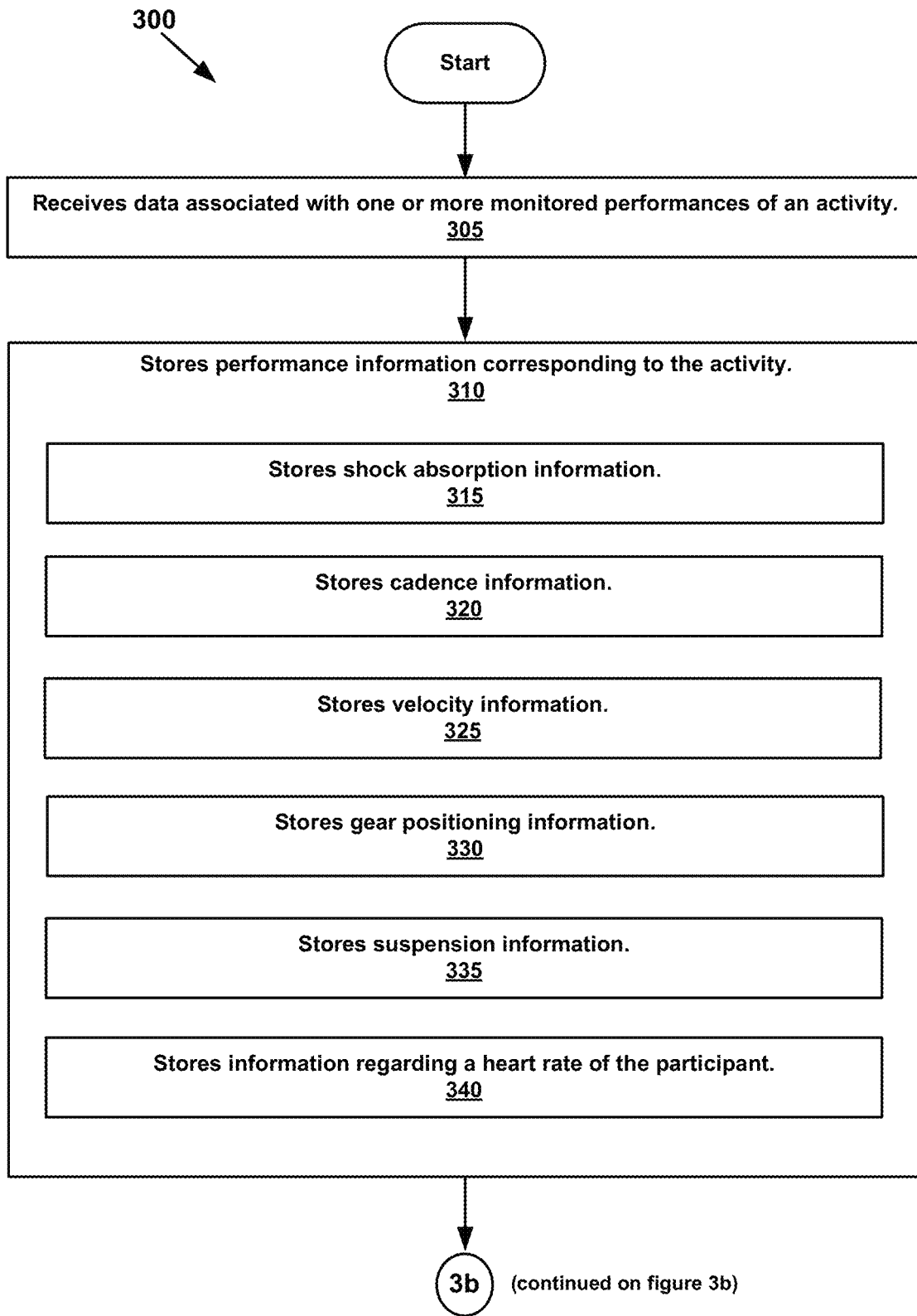
FIGS. 3a and 3b combine to form a flowchart 300 of an example method for performance comparison of multiple performances of an activity as disclosed herein.

In one embodiment of the present technology, data associated with one or more monitored performances of an activity is received at the digitally readable medium 205, as is described at 305 of FIG. 3a. In another embodiment, performance information corresponding to this activity is stored at the digitally readable medium 205, as is described at 310 of FIG. 3a. Then, comparative performance data is provided to a participant of the activity based on the comparison between the received data and the stored performance information, as is described at 345 of FIG. 3b.

For example, in one embodiment, once a course is registered, competitors can run the course on their own time, as long as they have a compatible and an authorized GNSS device. The trace of their competition run will be compared to the trace of the registered run to make sure the same exact course was run. Each new competitor is given an icon for that particular course.

A live run feature can be run on the website where the interested competitor can run their icon versus other chosen rider's icons down the course. In this manner, the interested competitor may interactively visualize at which point he/she is faster or the other riders are faster at specific sections of the course.

Figure 6:
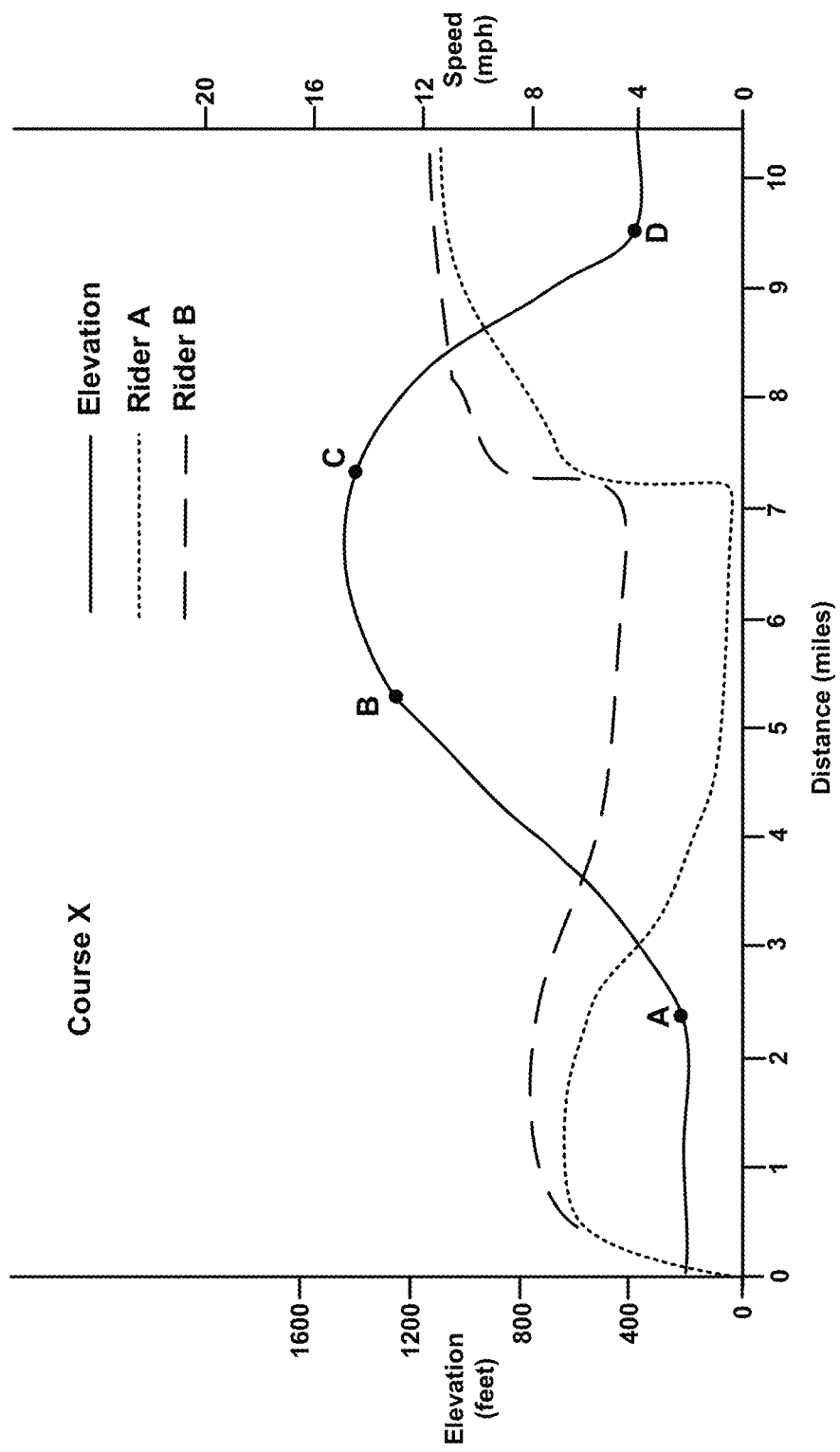
FIG. 6 is a graph measuring the speed, elevation and distance traveled by two bicycle riders as disclosed herein.
Figure 7:
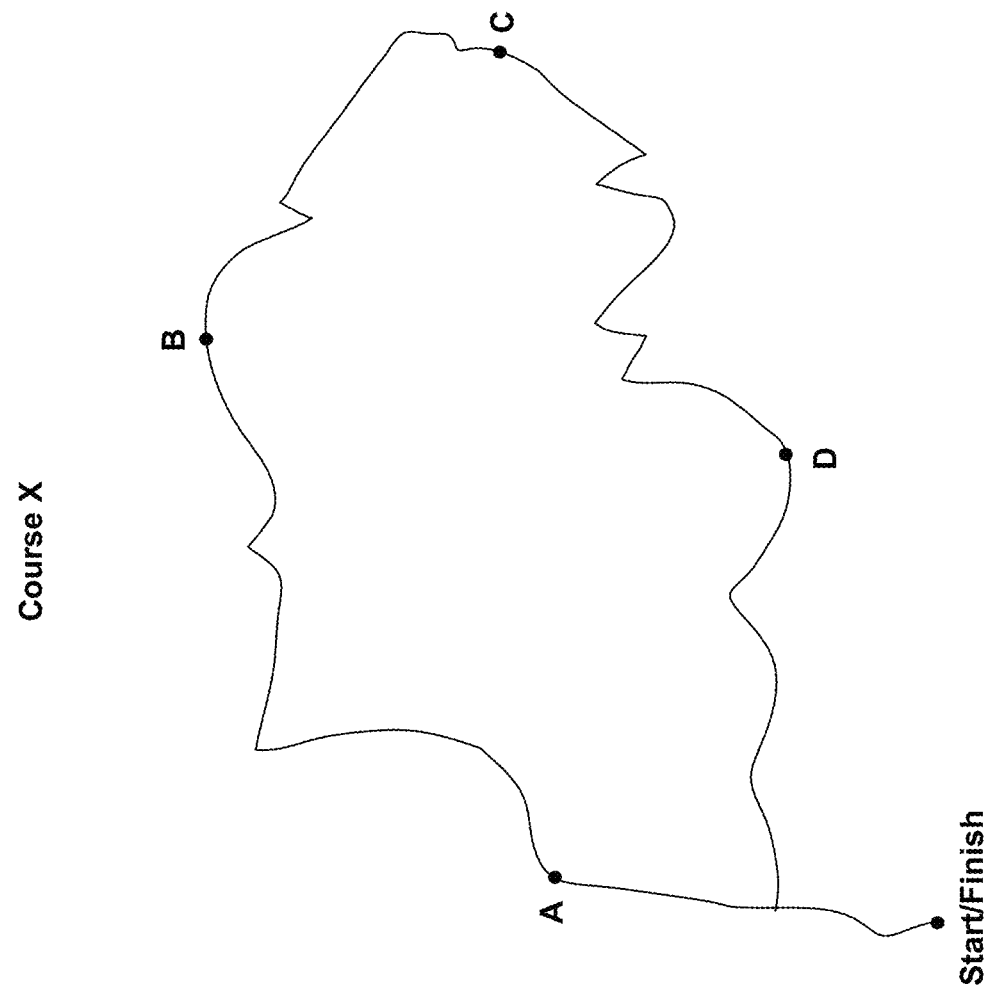
FIG. 7 is a trail map of the trail the two bicycle riders traversed as shown in FIG. 6 as disclosed herein.
Figure 7:
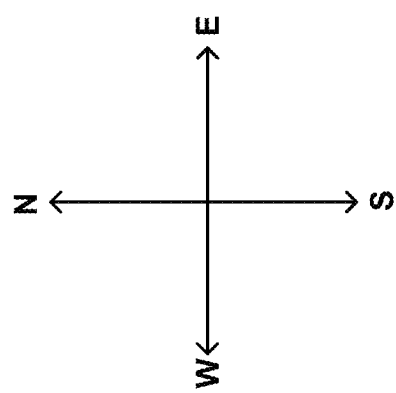

For example, and referring now to FIGS. 6 and 7, a map of a bicycle trail, Course "X", and a graph of the bicycle rides of Rider A and Rider B on Course "X" are shown. FIG. 6 considers the elevation, speed and distance traveled by the riders. Course "X" is a registered course. Rider A has an authorized GNSS device (a participant activity monitoring unit 105). Rider A rides the course. Rider A then uploads the data associated with his monitored ride performance onto a computer 210. Computer 210 communicates Rider A's Course "X" ride, either via wire or wirelessly, to the digitally readable medium 205. The digitally readable medium 205 compares Rider A's Course "X" ride to the registered Course "X" ride (not shown), to determine if Rider A stayed on Course "X" during his ride.

Furthermore, FIG. 6 also shows Rider B having also ridden Course "X" and having uploaded her information to a computer that communicates, wired or wirelessly, to the digitally readable medium 205. (Rider B also has an authorized GNSS device.) Rider A is now able to compare his ride to that of Rider B, and vice versa. Overall, Rider B finds that her ride was faster than Rider A's ride. As can be seen by the elevation vs. speed depiction in FIG. 6, Rider B was able to travel uphill at greater speeds than Rider A (between point "A" and point "C"). Furthermore, FIG. 6 shows that particular points along its graph, "A", "B", "C" and "D" match up with particular points, "A", "B", "C" and "D" on FIG. 7's Course "X" trail map. This point to point correspondence between the graph of FIG. 6 and the trail map of FIG. 7 enable a rider to determine his/her location within Course "X" itself.

Figure 3B:
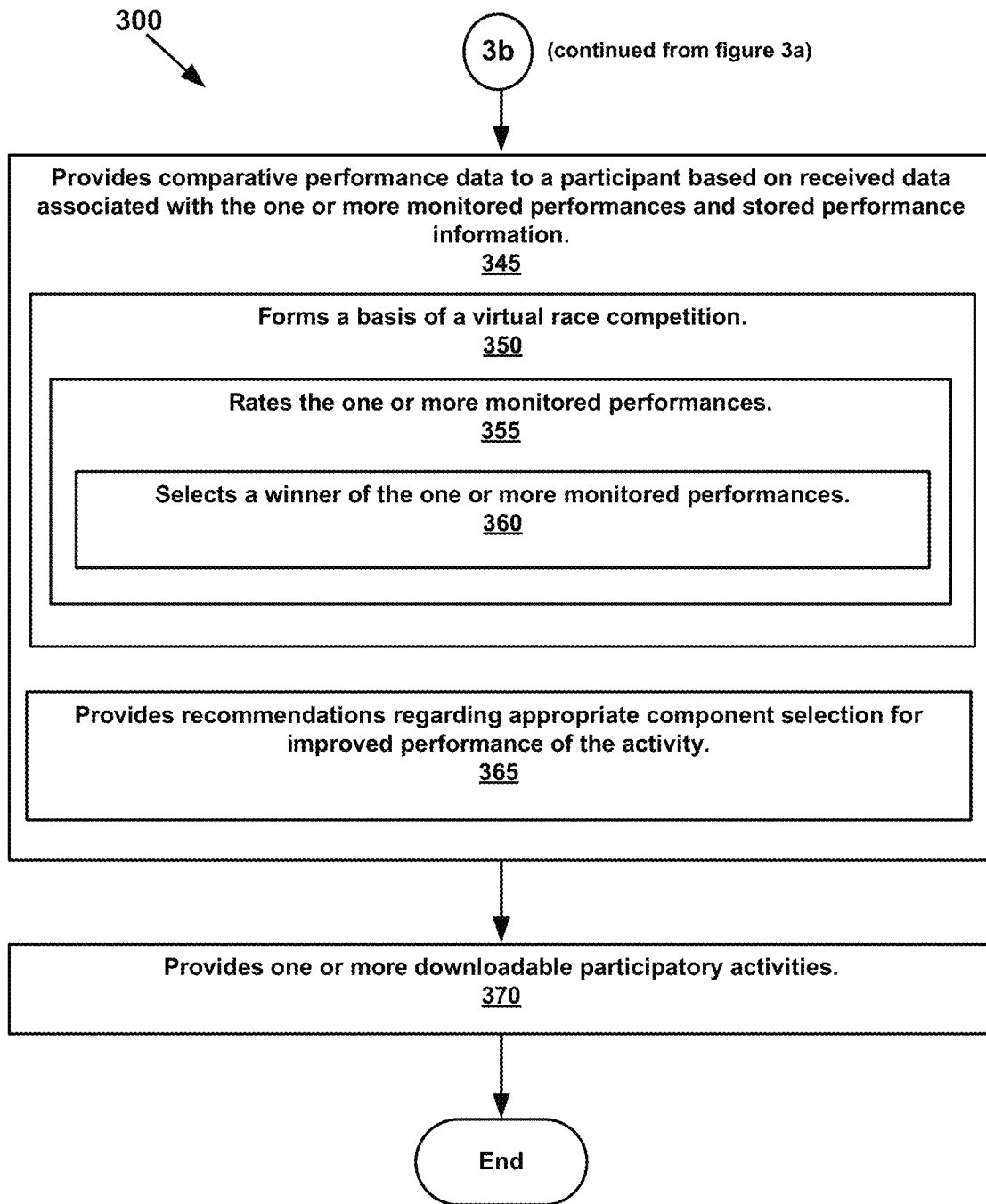

Additionally, and referring to 370 of FIG. 3b, one or more downloadable participatory activities is provided by the digitally readable medium 205. For example, in terms of mountain biking, a downloadable participatory activity is a course on which it is legal to mountain bike. It should be appreciated that a downloadable participatory activity may be any activity that is capable of being monitored by system 100. The digital readable medium 205 holds the course map and information relating to that course map for, such as but not limited to, data relating to an expert's ride through the course. In one embodiment, the participant 110 may download information relating to Course "Q" onto his/her system 100 at the activity information module 115. In this manner, participant 110 may use system 100 to enjoy riding Course "Q" without having to participate in a race with hundreds of other bicyclists. The participant 110 may also compare his/her ride to that of the expert's.

Referring now to 350 of FIG. 3b, some embodiments of the present technology form the basis of a virtual race competition, or as referred to herein, a "virtual race course" (VRC). In one embodiment, the VRC administrators will send out professional athletes with helmet cams and authorized GNSS devices to execute a fast course run time over a given registered course and to video the course during the run. Any course runner with access to a mobile GNSS can capture his or her own run of the given course and submit that to the internet website for posting. Over time, run data accumulates for given courses, and participants can compare their results with others who have run the course (including professionals). Additionally, participants can review specific paths or "lines" chosen by other competitors who submit video (e.g. helmet cam) course data with their run. In this way, the nonprofessional rider can compete head to head in the VRC world, and can review the line selection of the professional rider. In one embodiment, a single participant performs one or more monitored performances. In another embodiment, a plurality of participants performs one or more monitored performances. In one embodiment, a participant may run against their own performance or the performance of others by downloading the pre-recorded performance to system 100 prior to their ride. In one embodiment, a participant may "pre-ride" a course in virtual space by reviewing the pre-recorded ride data log, including video (and audio) of others. In one embodiment, a participant may critique his own ride by reviewing, on for example a home computer, the recorded ride data log.

A GNSS device, such as but not limited to, those manufactured by Garmin Ltd. or TomTom may be used. Other GNSS devices may also be used, such as those available with current mobile telephones (e.g. IPHONE by Apple, Inc. of Cupertino, California, United States). The GNSS devices are however equipped with an algorithm allowing storage of course information and the time data associated with the traversal of a designated course. One monitoring and recording system is described in U.S. Pat. No. 6,701,234, having inventor Andrew Vogelsang and incorporated herein by reference in its entirety. Other systems are described in U.S. Patent Application Publication Nos. 2009/0069972A1 assigned to Maritz Inc. and 2009/0070037A1 assigned to Maritz, Inc., each of which is incorporated herein, in its entirety, by reference. In one embodiment, the system disclosed herein derives course location data and associated speed/acceleration/altitude data (in one embodiment as a correlated data set) from algorithms within the GNSS.

Another monitoring and recording system is described in U.S. Pat. No. 7,415,336 assigned to Garmin, Ltd and incorporated herein by reference in its entirety. The GNSS of the present system is equipped to time and date stamp and "sign" with an encrypted verification code, data sets as they are generated. As such, in one embodiment, only verifiable data may be uploaded to the internet site (because the site screens incoming posts for verification codes generated by the recording GNSS device).

In one embodiment, a host website hosts many different types of courses and many different types of events. A user can be matched to a desired sport/competition or other relevant classification or sub-class of activity or location (or other) by answering an initial query (e.g. choosing an object from an object set identifying the activity and sub-activity) upon entering the website. One matching method is described in U.S. Pat. No. 5,828,843 assigned to Mpath Interactive, Inc. and incorporated herein by reference in its entirety.

Any form of competition may be adapted to use with the VRC network system as disclosed herein. Additionally, competitors may post their profiles and other pictures and videos as they prefer. The VRC network functions to facilitate not only competition among athletes with similar interests but also serves as a social and networking site in facilitating communication among competitors (including individually identified personal networks, such as but not limited to, FACEBOOK of Palo Alto, California, United States). Optionally, participants can operate in a virtual competition world using GNSS generated data or other profile data. (U.S. Pat. No. 6,219,045 assigned to Worlds, Inc. is incorporated herein by reference in its entirety.)

Another sport suited for use with the present technology is motocross. Motocross is a very popular sport. Open practice session track days are well attended, but many individuals shy away from the very confrontational aspects of real time track racing. Open practice "track days" are days held open by race courses in which no actual race is scheduled. Therefore, riders (or drivers) may pay a fee and run the course for practice and improvement. The intimidation of a starting gate with up to 40 riders all heading into the first turn together keeps many riders from competing on actual race days. A motocross rider not wishing to experience the full blown race with line up start may race virtually using VRC. The VRC administrator can register various motocross tracks so that all a rider needs is an authorized (e.g., equipped in accordance with the disclosure herein) GNSS device mounted on their motorcycle, and they can compete on their local course at their discretion regarding time and circumstances. Such competition data can then be uploaded to the web site for comparison against others on the same track.

Again, professional riders can post times that they have run on these local and regional tracks along with video taken from a helmet cam. Using embodiments herein, the local amateur can compete against the professional rider. Thus, any day the track is open and any time of that day, the competitor can log a course run. Examples of sporting events that can be held using the VRC as disclosed herein are, but not limited to, the following: road racing track days; off road motorcycle riding; sailing (e.g. point to point or course type regatta); skiing; snowboarding favorite runs; trail running; and swimming.

The VRC can also be utilized as a virtual gym. For those who do not wish to compete against others but want to keep accurate track of their workout progress, the VRC can be utilized as a training log (e.g., weight training). This application focuses more on the website and less on the enabled GNSS. A GNSS system may not be required.

In all cases, the VRC site can also tie all these competitors and training athletes together with tech tips, equipment reviews, set up tips, course reviews, racing line chat, training tips, etc. . . .

Popular courses with strong reviews can be visited by other enthusiasts from around the globe. The VRC system will seek travel and destination location activity from enthusiasts from around the world to tie in posting times and competition on courses they have only read about. In one embodiment, course run data, global position data and user generated video data are associated with a broader inquiry web site such as Google Earth of Google Inc. of Mountain View, California (or travel web sites) and users may virtually "ride" courses (or ski runs or experience the appropriate athletic endeavor virtually) before choosing to travel to them. Users "racing" or other athletic activity can be tied into vacation plans.

Established riding venues like destination bike parks can register specific runs and/or specific sections of favorite runs tied together. Vacation visitors can post times on these courses or propose new ones to the VRC system. This same thing applies to ski/snowboard areas. Amateurs can run (e.g. bike) sections of the Tour de France, and can compare their times to the stages and times actually raced.

Referring now to 355 of FIG. 3b, in one embodiment, one or more of the monitored performances is rated. Referring now to 360 of FIG. 3b, in another embodiment, a winner of the one or more monitored performances is selected. For example, the VRC for those groups wishing to take things further can establish qualifying events to end up with championships and champions. For example, the champions can be crowned for, but not limited to, the following: most rides in a given time; the most courses run in one year; the most vertical feet climbed; and the most vertical feet descended (altitude data component).

The VRC system will track stats on enthusiast user activity, which will be very marketable to product leaders in the various activities.

The VRC system is a huge business opportunity with vacation/travel companies, destination locations and Original Equipment and After Market manufacturers all vying for ad space in the VRC website. For example, a user will procure a GNSS equipped device that is further equipped with the capability of gathering course traversal data, corresponding time and corresponding altitude and generating a data set that is time date stamped and verified. The user will then enter the internet (or suitable network) and request a new course registration if applicable, or existing course add run if applicable. The user will upload a verified data set for the chosen course (following new course registration by the website if applicable) and any other peripheral information such as weather stats, course condition, comments, video, etc. The user may choose to create a personal profile space or add a link to her course run to her existing profile.

The upload process occurs via, for example, but not limited to, a Bluetooth (a standard and a communications protocol) link between the GNSS device and a personal computer/terminal of the user. The personal computer is in turn connected to the internet via a suitable connection medium. Optionally, the data is loaded into the computer (digitally readable medium such as hard drive) and uploaded to the internet at a later time. Following upload, the user may view her results as compared with others who have traversed the same course and may also post comments.

The course page itself includes a link whereby users can post comments, photos and other information regarding the course (e.g. a "blog"). Additionally, the website includes a larger general blog or blogs regarding various sporting types and topics. The website posts the users' latest results and queries other results from the same course and then files users in appropriate place ranking (e.g. based on the fastest run times). In one embodiment users may blog and post comments regarding their own or other users recorded data sets for given trails/runs. Other persons may now view the user.

Referring now to 365 of FIG. 3b, in one embodiment, recommendations regarding appropriate component selection for improved performance of an activity is provided. Furthermore, and referring to 315, 320, 325, 330, 335, and 340 of FIG. 3a, the following information may be stored at activity information module 115, respectively: shock absorption, cadence, velocity, gear positioning, suspension, and heart rate of the participant. (Of note, this is not an exhaustive list of possible information that may be stored.) For example, and referring again to FIGS. 6 and 7, based on the riding performance of Rider A throughout Course "X", recommendations geared towards improving Rider A's performance may be made. For instance, as can be seen on FIG. 6 with reference to Rider A, between the points "A" and "C", Rider A slowed significantly in the face of a steep uphill climb. In one embodiment, participant activity monitoring unit 105 also monitors factors such as gear positioning, the heart rate of the participant, calories burned, etc. . . .

Thus, an embodiment of the present technology may recommend, based on the Rider A's performance and stored data relating to gear positioning as well as elevation, velocity and distance, that Rider A should change up his/her gear positioning technique. Furthermore, a new gear, or suspension component, or tuning (e.g. adjustment) state may be recommended to Rider A as being easier to manipulate, thereby increasing Rider A's speed during ride time. Furthermore, embodiments of the present technology may recommend new shocks or related adjustments, based on Rider A's performance.

Figure 4:
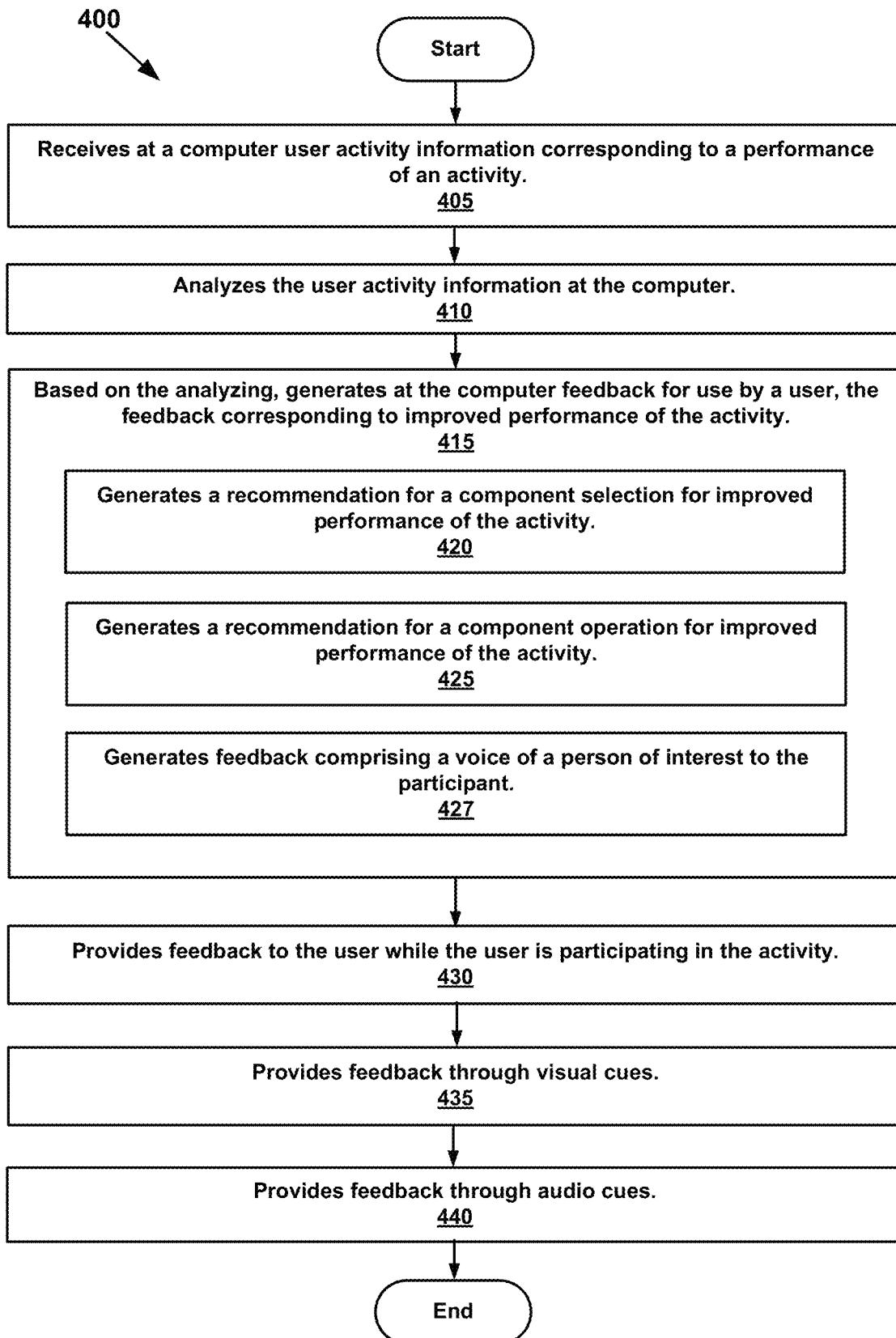
FIG. 4 is a flowchart 400 of an example method for enhancing revenue generation as disclosed herein.

Referring now to 400 of FIG. 4, a flowchart of a method for enhancing revenue generation is shown. Referring now to 405 of FIG. 4, in one embodiment, user activity information corresponding to a performance of an activity is received at a computer. Referring now to 410 of FIG. 4, in one embodiment, the user activity information is analyzed at the computer. Then, and referring to 415 of FIG. 4, based on the analyzing of 410, feedback is generated for use by the user at the computer. The feedback corresponds to improved performance of the activity.

For example, and referring to 420 of FIG. 4, feedback may comprise a recommendation for a component selection for improved performance of the activity. As described herein, this component selection may be for new shocks, an updated suspension system, alternate equipment, etc. Further, and referring to 425 of FIG. 4, feedback may comprises a recommendation for a component operation for improved performance of the activity. For example, a rider may be told that he/she should switch into higher or lower gears more quickly and at particular points in time during climbing and descending a steep hill in order to improve overall speed.

Referring now to 430 of FIG. 4, in one embodiment, the feedback is provided to the user while the user is participating in the activity. In one embodiment, the user receives the feedback directly from system 100. In another embodiment, the user receives feedback through a device local to the user for promulgation to the user. For example, the device may be, but is not limited to, an earpiece coupled with system 100 and configured for capturing sound from the system 100 and delivering that sound to the user. In one embodiment, and referring to 435 of FIG. 4, the feedback is provided through visual cues. In another embodiment, and referring to 440 of FIG. 4, the feedback is provided through audio cues.

In one embodiment, and referring to 427 of FIG. 4, the feedback that is generated comprises a voice of a person of interest to the participant. For example, the person of interest may be an admired professional of the activity, or a fan favorite. Additionally, the person of interest may be anyone whom the participant wants to hear speaking to him/her before, during or after the performance of the activity, within the limits of the technology of voicing over data, the manufacturing of system 100 and the designing of the digitally readable medium.

In one embodiment, for example, mountain biker Bob has never ridden any trails or raced any courses in Fantasia. He has heard, however, that the riding and racing in Fantasia is spectacular and challenging. He has heard of several race courses in Fantasia and he sits down at his home computer to check it out. He connects to a website that includes a user navigable global map (e.g. Google Earth) having icons associated with geographic locations thereon. He navigates to a map of Fantasia and specifically to a race course used for an annual mountain bike race called the "Skyline." There are many pre-recorded runs of Skyline associated with visible and active icons on the map. Bob selects an icon and a menu appears that includes choices such as: Ned Pete Skyline run no. 1 video, Ned Pete Skyline run no. 1 audio, Ned Pete Skyline run no. 1 altitude and location data, Ned Pete Skyline run no. 1 bike data, Ned Pete Skyline run no. 1 body data, Ned Pete Skyline run no. 1 Google earth terrain enhancement (option allowing terrain map data to enhance video data as needed to make the recording play complete), Select combination, All. Bob selects video, audio and altitude and location data. A menu then appears with the options "download" and "play." Bob selects play (had he selected "download" he would have been prompted to designate a destination for the files at which point he could have selected a system 100 connected to his home computer). Bob watches the video and listens to the audio of Ned's race run. While observing a screen-in-screen inset showing Ned's position on the race course trail map. Bob watches the video several times, so much so, that he feels he is getting the course "wired." Bob is gaining the mental experience and reinforcement, regarding the race course, without ever having ridden Skyline.

In one embodiment, for example, mountain biker Bob decides that he wants to participate in the annual mountain bike race, "Skyline". Skyline is a 20 mile race over varied terrain. Bob designs a training schedule for himself in preparation for the race, aided by the sage advice he has already heard from Ned Pete. To help himself with his training, Bob purchases from his local bike shop a system 100. Bob then connects his system 100 with a digitally readable medium (e.g. server on the internet) via his computer and downloads performance information relating to the Skyline race into his system 100. This performance information includes various data, instructions and pep talks from Ned Pete, a famous mountain bike racer.

In one embodiment, Bob attaches system 100 to his handlebars of his bicycle. Bob turns on his wireless earphone set that attaches to his helmet and also is configured to communicate (e.g. receive audio) with system 100.

Then, Bob's training begins. As Bob warms up by riding the one mile from his car to the beginning of the trail, he hears system 100, in the voice of Ned Pete, giving him a pep talk about the Skyline race. For example, Bob hears, "This is a very challenging race over really rough terrain, but I know that you can do it! I'll be with you at every turn. I'll tell you when you should hammer it and what gears to crank." Bob then makes it to the beginning of the trail. He stops his bike, sets his watch, and then starts. Immediately, he hears Ned say "Great start! Keep it moving . . . . You've got a sharp corner coming up to your left with a log. Bunny hop and kick-out to your right. The trail cuts down to the left . . . Great job. You're on target." Bob appears to have begun his trail ride with great success.

In one embodiment, Bob begins to pour it on early in the course and is running ahead of his "rabbit." Everything is looking good when suddenly Ned's voice alerts, "you need to slow up a bit because your current pace is unsustainable." Bob has a heart rate monitor and a power meter rear hub. The data from those devices compared with the current location on the Skyline run, allow system 100 to trigger an alert based on known physiology of Bob and/or of athletes generally or a suitable combination thereof (e.g. a human in good condition is capable of outputting a sustained approximately ½ horsepower. If Bob is dramatically exceeding a known physiological parameter or his heart rate is anaerobic or his blood oxygenation is dropping dramatically (with an oxygen sensor), the system 100 might assume it was an end race sprint. The system 100, however, will alert Bob if he is too far from the end to sustain his activity level though the remaining course).

Later on in the ride, Bob starts to fall behind his chosen "rabbit" pace. System 100 has calculated the difference between the rabbit and Bob's performance and when the difference reached a predetermined (e.g. chosen by Bob) threshold it triggered an audio signal. He hears Ned state, "Get moving! You're falling behind. Simultaneously, a red light illuminates on the face of system 100 making it clear that Bob is behind his "rabbit" pace. "Pay attention to your gears and your pedaling. You've got about half a mile of downhill coming up. Let's make up time. Lots of jumps. Get big air." Later on, Bob hears, "You're dialed in! Great job" Concurrently, the light on his system 100 is glowing green indicating he is even with the pace. Bob finishes the trail course in fairly good time, two and one-half hours. Bob then goes home and downloads the data associated with his monitored performance to the website. The next Saturday, Bob plans on riding that same course again, and comparing the new results with his time of two and one-half hours.

In one embodiment, system 100 may already have Ned Pete's voice with stored instructions that are ready for delivery to a participant. In another embodiment, these instructions may be downloaded to system 100 from remote server accessed using the Internet. Furthermore, there may be instructions and advice for various skill-levels of a participant, such as beginner, intermediate and advanced.

Thus, embodiments of the present technology enable the participant to receive instructions from famous people associated with the activity while contemporaneously performing the activity. Furthermore, these instructions may come in the form of the vernacular associated with the activity, thus making the instructions more enjoyable to listen to and ultimately more relevant to the participant.

Figure 5:
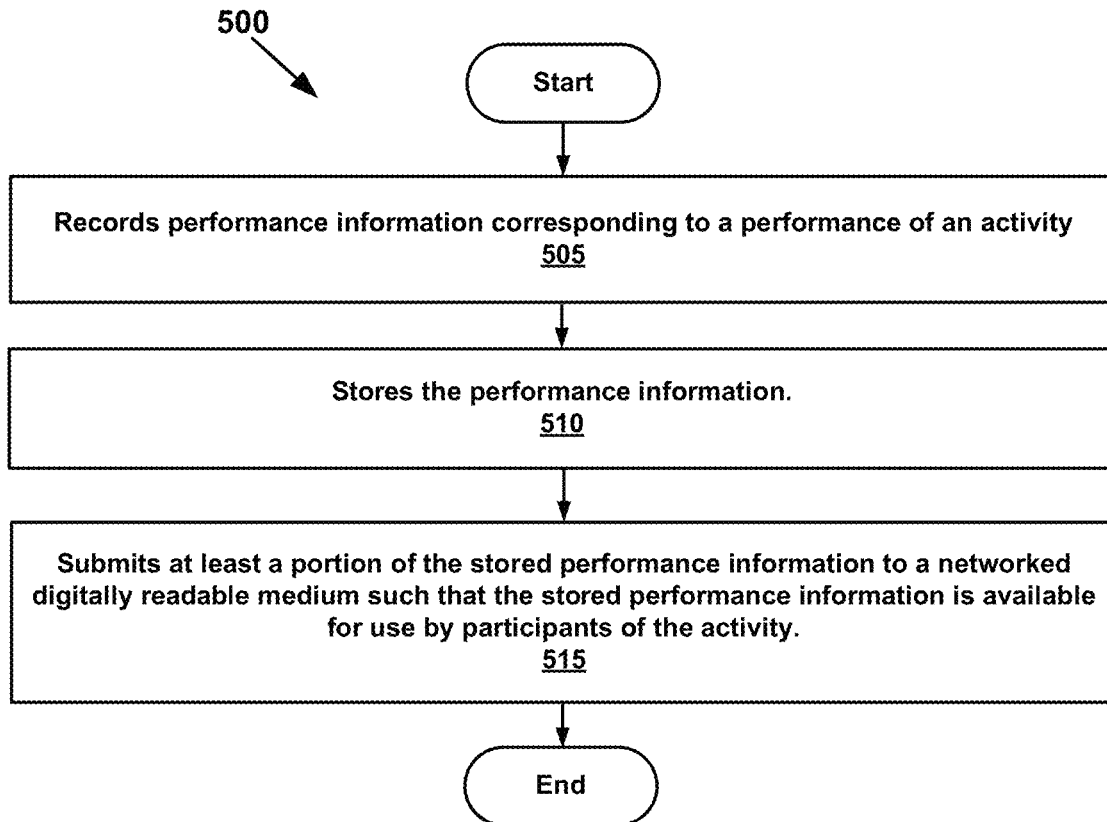
FIG. 5 is a flowchart 500 of an example method for participating in an activity as disclosed herein.

Referring now to 500 of FIG. 5, a method for virtually competing is shown. Referring now to 505 of FIG. 5, performance information corresponding to a performance of an activity is recorded. In one embodiment, different performances of the activity are recorded. The same participant or a combination of different participants may record performance information. In one embodiment, this performance information is recorded on system 100.

Referring now to 510 of FIG. 5, in one embodiment, the performance information is stored to a memory. In one embodiment, the memory resides on system 100. In another embodiment, and referring to 515 of FIG. 5, at least a portion of the stored performance information of 510 is submitted to a networked digitally readable medium such that the stored performance information is available for use by participants of the activity. In one embodiment and as described herein, the digitally readable medium generates a rating for the performance of the activity compared to other submitted performances of the activity. In yet another embodiment and as described herein, the networked digitally readable medium determines a winner of the submitted performances of the activity. In one embodiment and as described herein, the networked digitally readable medium provides recommendations regarding appropriate component selection for improved performance of the activity. In yet another embodiment and as described herein, the networked digitally readable medium stores performance information corresponding to, but not limited to, one or more of the following: shock absorption; cadence; velocity; gear positioning; suspension; participant's heart rate; power; time; breaking; cornering speed; and calories burned.

Thus, embodiments of the present technology enable multiple performances of the same activity to be compared against each other. Further, embodiments enable a method for enhancing revenue generation by recommending appropriate component selection to improve a participant's performance. Moreover, embodiments of the present technology enable a method for virtually competing is an activity.

Example Computer System Environment

Figure 8:
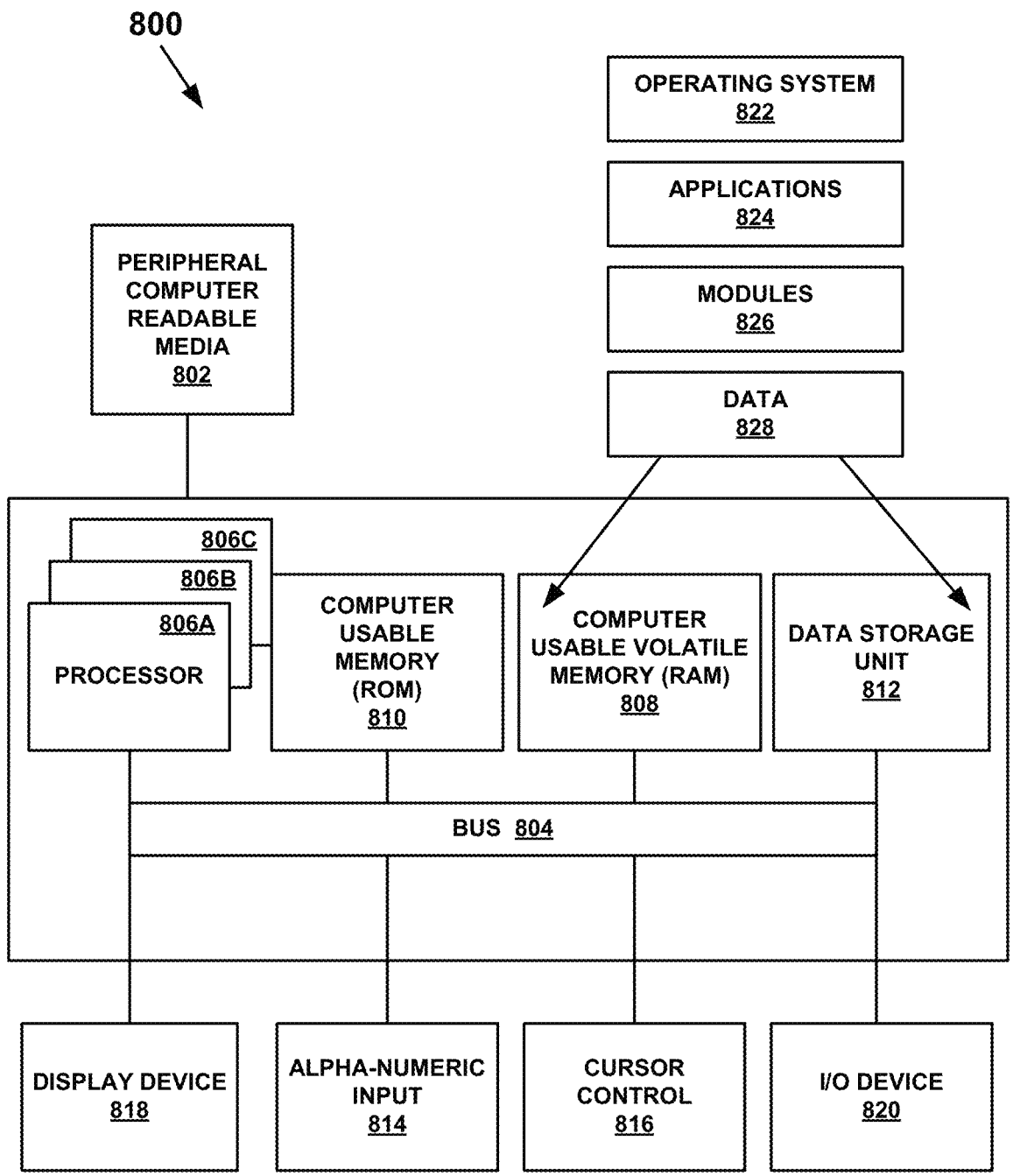
FIG. 8 is a diagram of an example computer system enabling performance comparison of multiple performances of an activity, as disclosed herein.

FIG. 8 illustrates an example computer system 800 used in accordance with embodiments of the present technology. It is appreciated that system 800 of FIG. 8 is an example only and that embodiments of the present technology can operate on or within a number of different computer systems including general purpose networked computer systems, embedded computer systems, routers, switches, server devices, user devices, various intermediate devices/artifacts, stand alone computer systems, and the like. As shown in FIG. 8, computer system 800 is well adapted to having peripheral computer readable media 802 such as, for example, a compact disc, and the like coupled therewith.

System 800 of FIG. 8 includes an address/data bus 804 for communicating information, and a processor 806A coupled to bus 804 for processing information and instructions. As depicted in FIG. 8, system 800 is also well suited to a multi-processor environment in which a plurality of processors 806A, 806B, and 806C are present. Conversely, system 800 is also well suited to having a single processor such as, for example, processor 806A. Processors 806A, 806B, and 806C may be any of various types of microprocessors. System 800 also includes data storage features such as a computer usable volatile memory 808, e.g. random access memory (RAM), coupled to bus 804 for storing information and instructions for processors 806A, 806B, and 806C.

System 800 also includes computer usable non-volatile memory 810, e.g. read only memory (ROM), coupled to bus 804 for storing static information and instructions for processors 806A, 806B, and 806C. Also, present in system 800 is a data storage unit 812 (e.g., a magnetic or optical disk and disk drive) coupled to bus 804 for storing information and instructions. System 800 also includes an optional alphanumeric input device 814 including alphanumeric and function keys coupled to bus 804 for communicating information and command selections to processor 806A or processors 806A, 806B, and 806C. System 800 also includes an optional cursor control device 816 coupled to bus 804 for communicating user input information and command selections to processor 806A or processors 806A, 806B, and 806C. System 800 also includes an optional display device 818 coupled to bus 804 for displaying information.

Referring still to FIG. 8, optional display device 818 of FIG. 8 may be a liquid crystal device, cathode ray tube, plasma display device or other display device suitable for creating graphic images and alpha-numeric characters recognizable to a user. Optional cursor control device 816 allows the computer user to dynamically signal the movement of a visible symbol (cursor) on a display screen of display device 818. Many implementations of cursor control device 816 are known in the art including a trackball, mouse, touch pad, joystick or special keys on alpha-numeric input device 814 capable of signaling movement of a given direction or manner of displacement. Alternatively, it will be appreciated that a cursor can be directed and/or activated via input from alpha-numeric input device 814 using special keys and key sequence commands.

System 800 is also well suited to having a cursor directed by other means such as, for example, voice commands or haptic movement. System 800 also includes an I/O device 820 for coupling system 800 with external entities.

Referring still to FIG. 8, various other components are depicted for system 800. Specifically, when present, an operating system 822, applications 824, modules 826, and data 828 are shown as typically residing in one or some combination of computer usable volatile memory 808, e.g. random access memory (RAM), and data storage unit 812. However, it is appreciated that in some embodiments, operating system 822 may be stored in other locations such as on a network or on a flash drive; and that further, operating system 822 may be accessed from a remote location via, for example, a coupling to the internet. In one embodiment, the present invention, for example, is stored as an application 824 or module 826 in memory locations within RAM 808 and memory areas within data storage unit 812.

Computing system 800 is only one example of a suitable computing environment and is not intended to suggest any limitation as to the scope of use or functionality of embodiments of the present technology. Neither should the computing environment 800 be interpreted as having any dependency or requirement relating to any one or combination of components illustrated in the example computing system 800.

Embodiments of the present technology may be described in the general context of computer-executable instructions, such as program modules, being executed by a computer. Generally, program modules include routines, programs, objects, components, data structures, etc., that perform particular tasks or implement particular abstract data types. Embodiments of the present technology may also be practiced in distributed computing environments where tasks are performed by remote processing devices that are linked through a communications network. In a distributed computing environment, program modules may be located in both local and remote computer-storage media including memory-storage devices.

RECREATING A PERFORMANCE OF AN ACTIVITY FROM A CAMERA PERSPECTIVE

More generally, in embodiments of the present technology, a performance of an activity is recreated from a camera's perspective. For example, a camera is coupled with a participant during an activity. This camera generates a video feed of the performance of the activity. In one example, the activity being performed is mountain biking. While the following explanation refers to mountain bike riding, embodiments are not limited to such an activity.

A GNSS is used to map the trail traversed by the mountain biker. The actual video taken by the camera is then correlated with the GNSS altitude and map log to create (in a computer or on the web) a real time recreation of a ride from the camera's perspective with enhanced effects based on the GNSS data (e.g., altitude and map log). In one embodiment, the video camera is equipped with a GPS marker feed from the GNSS (GPS unit) and digital GPS data is placed in the digital video feed at the GPS sampling rate (e.g. user designated or by location differentiation and change rate based sampling or other suitable sampling rate). The GNSS comprises a transmitter for transmitting location and altitude data and the video camera marker feed comprises a receiver for receiving data from the GNSS. The marker feed further comprises a data buffer, a processor and suitable video correlation software. The marker feed may be wired or preferably wireless and the GPS data may be associated with the video along with date time data generated by the video camera. In one embodiment the marker feed comprises a real time pairing buffer in which video data temporarily resides while corresponding GPS is associated with corresponding "frames" or video sectors.

In one embodiment, the mountain biker carries a display screen, coupled with the camera, that shows a split screen graphic showing the altitude and map aside the rider perspective video. As described herein, training recommendations may be included on the display screen or through audio cues.

The GNSS data together with the rider perspective video ("data pack") may then be correlated with a global map system so that the data pack may be tied to the actual location of the participant's performance. One example of a global map system is GOOGLE EARTH of Google, Inc. of Mountain View, CA. Mountain bike riders are then able to "shop" on line for riding venues that they may wish to visit.

The GNSS and global map system data may also be used to augment the video data when video is missing. For example, if only segments of a rider were actually taped, intervening portions may be interpolated and graphically simulated using the global map system and/or the actual GNSS data. In this manner, an interested party may view a virtual composite ride of their own designation comprising elements of real video and simulated video. In one embodiment, a processor ties various pre-recorded ride segment together to form a user chosen trail map and presents the segment data in a coherent and continuous fashion as if the chosen trail data had been contiguously generated.

Figure 9:
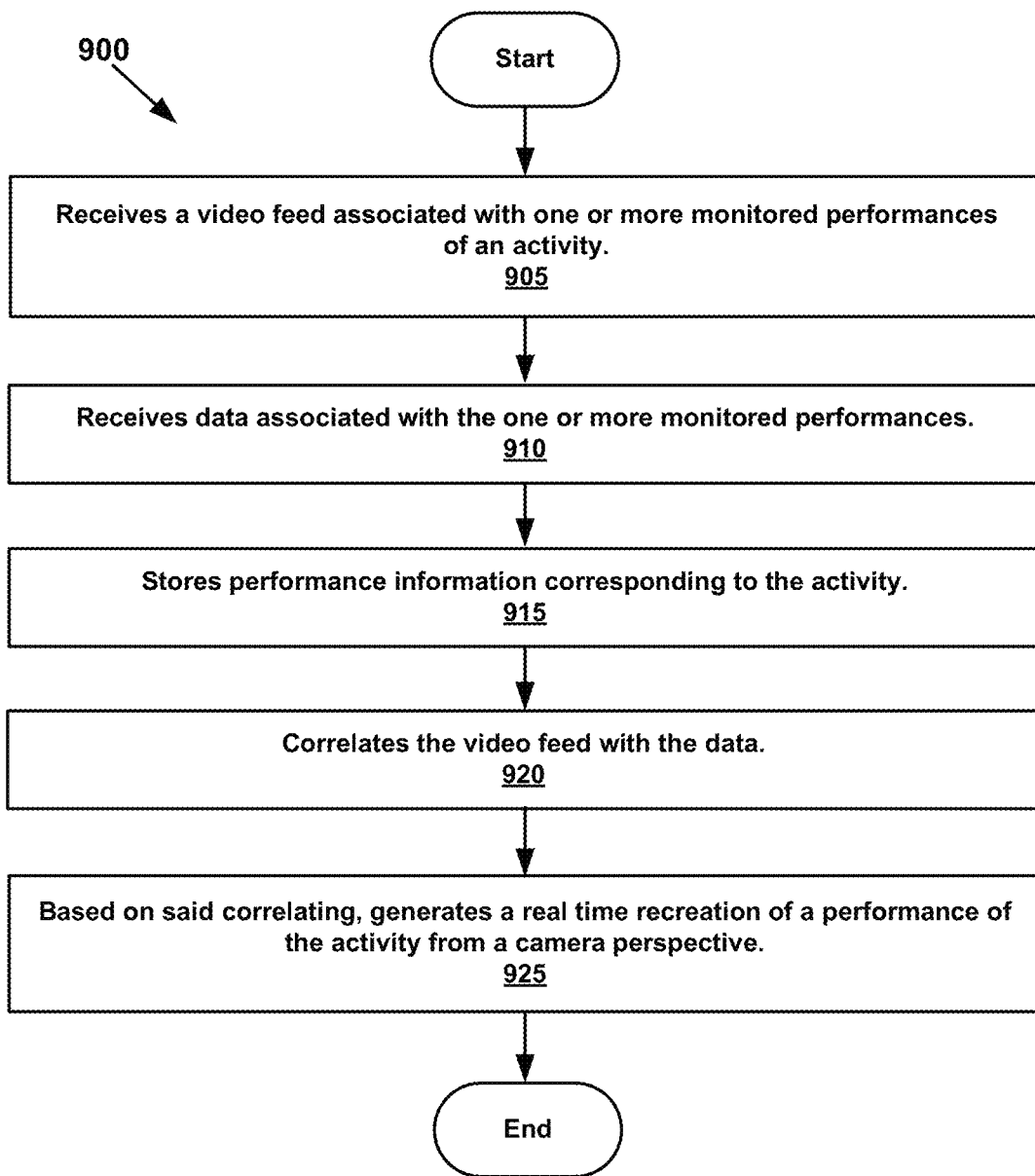
FIG. 9 is a flowchart 900 of an example method for recreating a performance of an activity from a camera perspective, as disclosed herein.

Referring now to FIG. 9, a flowchart 900 of an example method for recreating a performance of an activity from a camera perspective is shown. Referring now to 905 of FIG. 9, a video feed associated with one or more monitored performances of an activity is received. The video feed may originate from any type of camera that may take video and is capable of being coupled with a participant while performing the activity.

Referring now to 910 of FIG. 9, in one embodiment and as described herein, data associated with the one or more monitored performances is received. Referring now to 915 of FIG. 9, in one embodiment and as described herein, performance information corresponding to the activity is stored. Referring now to 920 of FIG. 9, in one embodiment, the video feed is correlated with the data. Referring now to 925 of FIG. 9, in one embodiment, based on the correlation, a real time recreation of a performance of the activity is generated from a camera's perspective.

In one embodiment, a rider perspective video is presented to a participant. However, in another embodiment, a split screen graphic showing an altitude and map aside the rider perspective video is presented to a participant. In one embodiment, the real time recreation of a ride from a camera perspective is correlated with a global map system (e.g., GNSS) such that the correlated video feed and the data is linked to a real location.

In one embodiment, and as described herein comparative performance data is provided to a participant based on the received data associated with the one or more monitored performances and the stored performance information. In one embodiment, a recommendation corresponding to the improved performance of the activity is provided. In another embodiment, a recommendation for an appropriate component selection for improved performance of the activity is generated. In yet another embodiment, a recommendation for a component operation for improved performance of the activity is generated. As disclosed herein, in one example, feedback to a user is provided while the user is participating in the activity. This feedback to a user may comprise a voice of a person of interest to the participant. The feedback to the user may be through generated visual cues. The feedback to the user may also be through generated audio cues.

In another embodiment and as described herein, the comparative performance forms a basis of a virtual race competition. In yet another embodiment and as described herein, one or more of the monitored performances is rated.

In one example and as described herein, one or more downloadable participatory activities is provided. In another example, a global map system is used to augment the video feed associated with the one or more monitored performances of the activity by interpolating and graphically simulating a portion of the video feed of the activity that is missing.

In one embodiment of the present technology, a video recording apparatus comprises: a aperture for directing optical wavelengths; an optical to digital transducer in a path of the wavelengths; a wireless receiver having communication protocol instructions; an antenna connected to the wireless receiver; a memory having correlation instructions for correlating data received by the receiver with digital output from the optical to digital transducer; and a processor for running the correlation instructions. Some data correlation features are disclosed in U.S. Pat. Nos. 7,558,574 and 7,558,313 having inventors Feher and Kamilo, each of which is incorporated herein by reference. Some data correlation features are disclosed in U.S. Pat. Nos. 7,558,574 and 7,558,313, each of which is incorporated herein by reference.

While the foregoing is directed to embodiments of the present invention, other and further embodiments of the invention may be devised without departing from the scope thereof, and the scope thereof is determined by the claims that follow.

What is claimed is:

1. A system configured to be coupled with a participant of a sporting activity, said system comprising:

a participant activity monitoring unit configured for monitoring a performance of said sporting activity by said participant, wherein the sporting activity involves use of equipment, having one or more component that can be selected and/or tuned, and for determining a location of said participant during said sporting activity and outputting geographic position data indicating said location;

an activity information module configured for storing performance information corresponding to said sporting activity;

a participant performance correlator configured for delivering comparative performance data based on monitored performance of said sporting activity by said participant and stored performance information; and a feedback module configured for providing information to said participant based on said comparative performance data, said system configured to correlate said stored performance information associated with said performance of the sporting activity with the geographic position data of said equipment during the activity, said information provided by said feedback module comprises recommendations regarding appropriate component selection or component tuning for improved performance of said sporting activity, which recommendations are based on said geographic position data, wherein said recommendations regarding appropriate component selection recommend a component selected from the group consisting of: a new shock and an updated suspension system.

* * * * *